United States Patent [19]

Fukukita et al.

[11] Patent Number: 4,844,082

[45] Date of Patent: Jul. 4, 1989

[54] ULTRASONIC EXAMINATION APPARATUS

[75] Inventors: Hiroshi Fukukita; Shinichiro Ueno, both of Tokyo; Tsutomu Yano; Nobuaki Furuya, both of Kawasaki, all of Japan

[73] Assignee: Matsushita Electric Industrial Co., Ltd., Japan

[21] Appl. No.: 153,403

[22] Filed: Feb. 8, 1988

[30] Foreign Application Priority Data

Feb. 9, 1987 [JP] Japan .................................. 62-27731
Mar. 13, 1987 [JP] Japan .................................. 62-59409
Aug. 28, 1987 [JP] Japan ................................. 62-215630
Aug. 28, 1987 [JP] Japan ................................. 62-215631

[51] Int. Cl.$^4$ .............................................. A61B 8/00
[52] U.S. Cl. .................................. 128/660.06; 73/599
[58] Field of Search .................. 128/660; 73/597–599, 73/602, 625–626

[56] References Cited

U.S. PATENT DOCUMENTS

| 4,610,255 | 9/1986 | Shimura et al. | 128/660 |
| 4,633,883 | 1/1987 | Matsui | 128/660 |
| 4,679,565 | 7/1987 | Sasaki | 128/660 |
| 4,700,571 | 10/1987 | Okazaki | 73/597 |
| 4,754,760 | 7/1988 | Fukukita et al. | 128/660.06 |

FOREIGN PATENT DOCUMENTS 0147955 7/1985 European Pat. Off. ....... 128/660.06

OTHER PUBLICATIONS

Journal of Statistical Physics, vol. 36, Nos. 5/6, 1984, pp. 779–786 by Bruce J. West et al.
Japanese Journal of Applied Physics/Supplement, vol. 26, Supplement 26-1, 1987, Proceedings of 7th Symposium on Ultrasonic Electronics, Kyoto, 1986, pp. 49–51, Tokyo, JP; H. Fukukita et al.: "Application of nonlinear effect to ultrasonic pulse reflection method—Modulation characteristics of received pulse".
Ultrasonic Imaging, vol. 7, 1985, pp. 49–59, Academic Press, Inc., New York, US; T. Sato et al.: "Nonlinear parameter tomography system using counterpropagating probe and pump waves".
Journal of the Acoustical Society of America, vol. 80, No. 1, Jul. 1986, pp. 28–32, Acoustical Society of America, New York, US; C. A. Cain: "Ultrasonic reflection mode imaging of the nonlinear parameter B/A: I. A theoretical basis".

Primary Examiner—Francis Jaworski
Attorney, Agent, or Firm—Lowe, Price, LeBlanc, Becker & Shur

[57] ABSTRACT

The present invention relates to an ultrasonic examination apparatus which transmits ultrasonic waves into a body to be examined and receives the echo signals therefrom for examination of the inside of the body. The ultrasonic examination apparatus measures acoustic characteristics such as nonlinear parameter within the body using the fact that the characteristic of the reception ultrasonic wave from the inside of the body is varied in accordance with variation of the characteristics within the body. The ultrasonic examination apparatus has first and second ultrasonic transducers for transmitting first ultrasonic pulse and second ultrasonic pulse, respectively. The frequency of the second ultrasonic pulse from the second ultrasonic transducer is higher than that of the first ultrasonic transducer. The first and second ultrasonic pulses are superimposed and transmitted into the body. The phase relation of the first and second ultrasonic pulses is controlled so that the modulation characteristic of the reception signal based on the non-linear effect assumes the maximum.

23 Claims, 15 Drawing Sheets

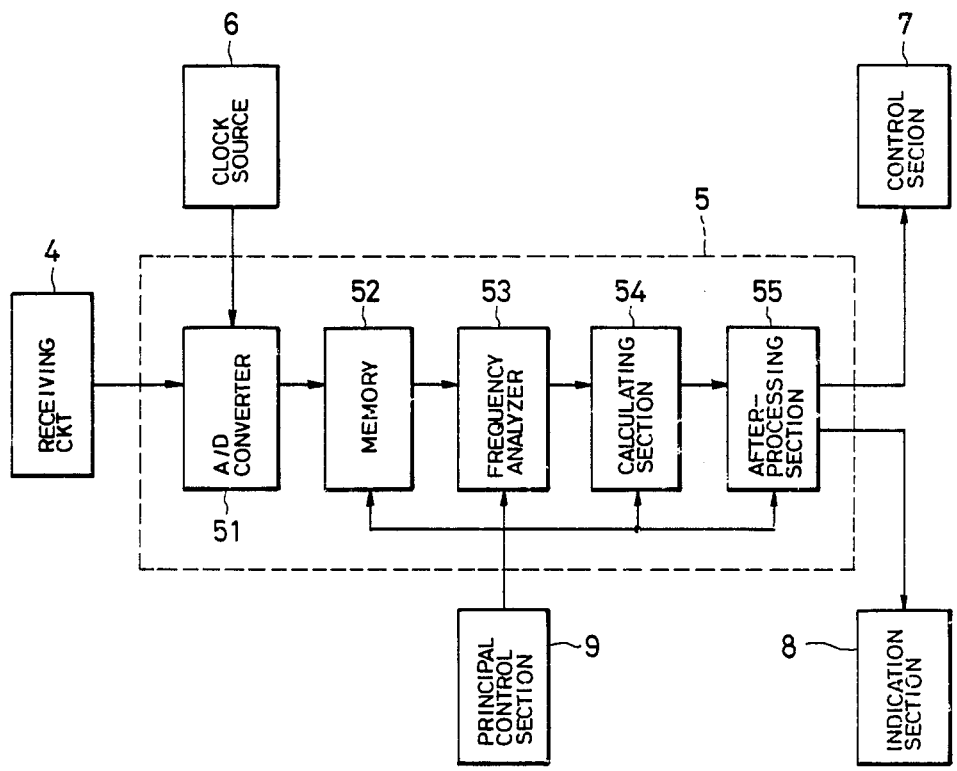

FIG. 3
(a) 
(b) 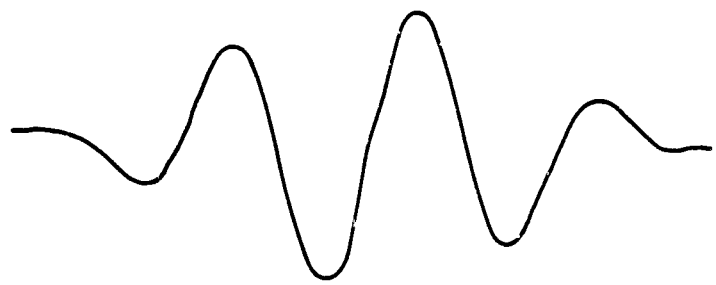
(c) 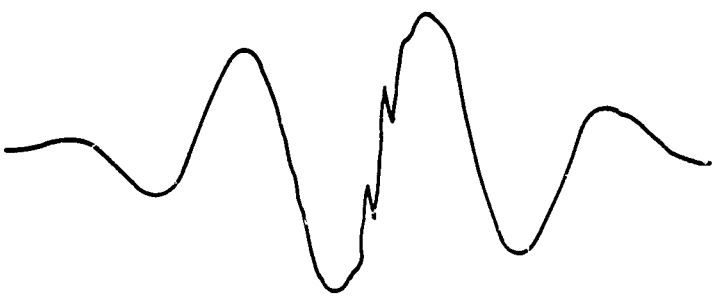
(d) 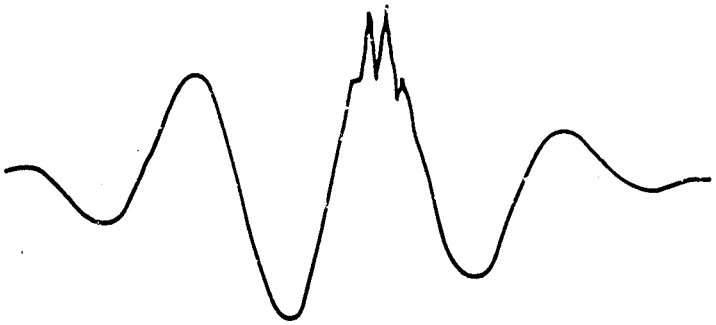

FIG. 4
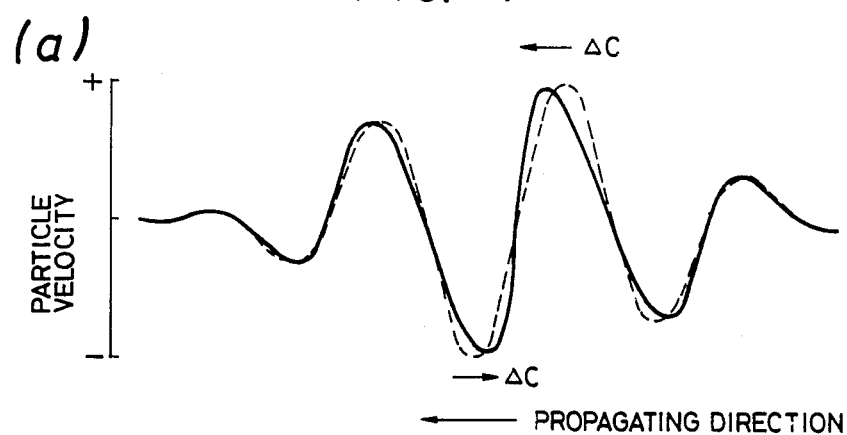
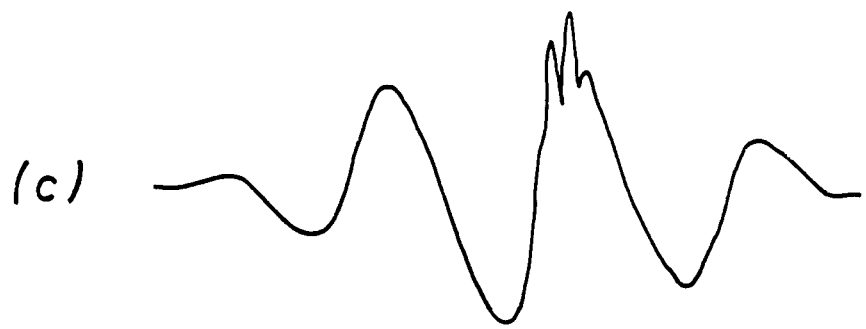

FIG. 8
(a)
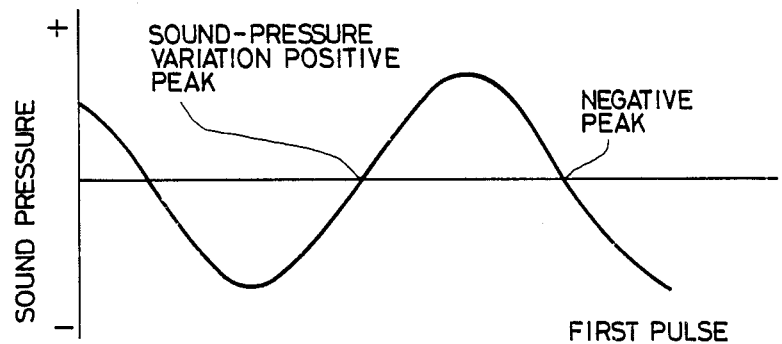
FIRST PULSE
(b)
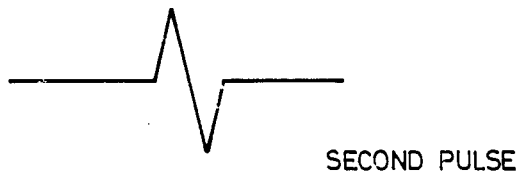
SECOND PULSE

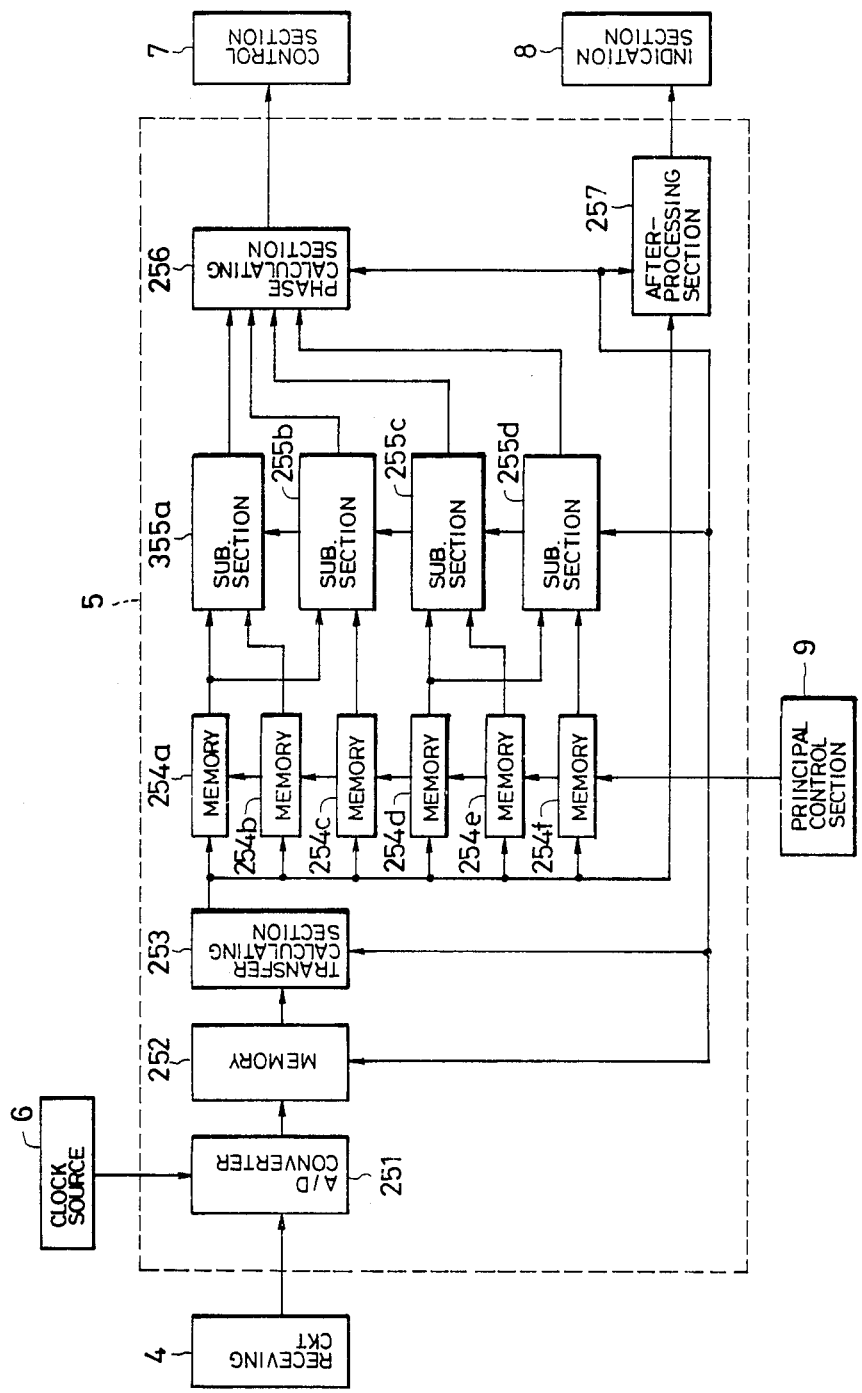

ULTRASONIC EXAMINATION APPARATUS

BACKGROUND OF THE INVENTION

The present invention relates to an ultrasonic examination apparatus for transmitting and receiving an ultrasonic wave toward and from a body to be examined in order to examine the inside of a body using the fact that the acoustic characteristic of the received ultrasonic wave is varied in accordance with the propagation characteristic within the body to be examined.

Known as a system to obtain acoustic information within a body to be examined is an ultrasonic diagnostic system which is principally of the pulse reflection type that is generally arranged to transmit an ultrasonic wave into an organism (body to be examined) and obtain the acoustic information within the organism on the basis of the echo wave from the inside of the organism. The pulse reflection system generally obtain a cross-sectional image of the body by two-dimensionally collecting and indicating information within the organism obtainable on the basis of the magnitude of the reflection echo, i.e., amplitude value and propagation time of the ultrasonic wave, from boundary surfaces with different acoustic impedances. Recently, the ultrasonic diagnostic apparatus, in addition to judgement of the configuration of the organism tissue, is further required to obtain information relating to the quality thereof. Such information relating to the quality can be obtained, for example, by measuring the degree of attenuation, the acoustic velocity, the acoustic non-linear parameter and/or the like which are inherent to various internal organs within the organism. In the case of measurement of the non-linear parameter B/A, the following relational expression may be used basically.

$$\Delta C = (1 + B/2A) \cdot v \qquad (1)$$

where v is the particle velocity of the acoustic wave, B/A is the acoustic non-linear parameter of a medium and $\Delta C$ represents the variation of the acoustic velocity based upon the non-linear effect.

It will be understood from the equation (1) that the acoustic velocity is increased when the direction of the particle velocity of the acoustic wave is coincident with the advancing direction of the acoustic wave and the acoustic velocity is reduced when reversed thereto, resulting in distortion of the waveform of the acoustic wave. For measuring this distortion of the waveform, conventional apparatus have been arranged to transmit an ultrasonic wave into a body to be examined, analyze the distortion of the obtained reception signal and perform comparison of the levels of the higher harmonic components for estimation of the non-linear parameter.

There is a problem which arises with this type of distortion-measuring apparatus, however, in that the error is essentially great in the case of obtaining the non-linear parameter from the higher harmonic component of the pulse-echo reception signal for a medium such as an organism in which the attenuation of the ultrasonic wave is greater and the attenuation characteristic depends upon the frequency, thereby resulting in occurrence of frequency dispersion of the acoustic velocity.

Furthermore, known as another example to obtain the information within the body using an ultrasonic wave is a non-destructive examination system which is arranged to transmit an ultrasonic wave into a structure and to obtain information in the inside of the structure on the basis of the reflection wave from the inside thereof. This is similarly arranged so as to obtain a cross-sectional image of the body by two-dimensionally collecting and indicating information within the structure obtainable on the basis of the magnitude of the reflection echo, i.e., amplitude value and propagation time of the ultrasonic wave, from boundary surfaces with different acoustic impedances. Recently, it is also required that the non-destructive examination system, in addition to the examination of defects and so on based upon the configuration of the inside of the structure, obtains information relating to the quality of the materials making up of the structure. Such information relating to the quality of the material can be obtained, for example, by measuring the propagation characteristic of the ultrasonic wave or the scattering property within the structure. In the case of measuring the ultrasonic wave propagation characteristic or the ultrasonic wave scattering characteristic in accordance with the pulse reflection method, as will be described hereinafter, difficulty would be encountered to independently measure one or both the characteristics. The ultrasonic wave propagation characteristic, particularly the ultrasonic attenuation characteristic, and the ultrasonic scattering characteristic are in closed relation to each other as described in "Journal of Statistical Physics", Vol. 36, Nos. 516, Pages 779 to 786 published in 1984. On the other hand, if there is the possibility to independently obtain the ultrasonic propagation characteristic and the ultrasonic scattering characteristic, the possibility may result in quantitatively understanding the quality of the material, particularly polycrystal portion of a metal and the like or the quality of the defect portion or the like within a sintered body. The conventional method of measuring the ultrasonic propagation characteristic will be described hereinbelow with reference to FIG. 1 for a better understanding.

In FIG. 1, numeral 101 represents a body to be examined and numeral 102 designates an ultrasonic transducer for transmitting an ultrasonic wave into the body 101 and receiving the ultrasonic wave reflected from the inside of the body 101. Between the body 101 and the ultrasonic transducer 102 is provided a coupling medium 103 for performing an acoustic coupling therebetween which is encased in a container 104. The ultrasonic transducer 102 is driven by a pulse driver 105 and also coupled to a receiving section (preamplifier) 106 for amplifying the signal received thereby which is in turn coupled to a detector 107 for demodulating the output of the receiving section 106. Numeral 108 is a scan transducing section for storing the output of the detector 107 so as to form a cross-sectional image, followed by an indication section 109 for indicating the output of the scan transducing section 108. The receiving section 106 is also coupled to a signal analysis section 110 for performing the frequency analysis with respect to the output of the receiving section 106, the output of which is supplied to the scan transducing section 108 and indicated at the indication section 109.

In operation of the apparatus thus arranged, the pulse driver 105 initially generates a drive pulse signal which is supplied to the ultrasonic transducer 102 to produce an ultrasonic pulse. The ultrasonic pulse from the ultrasonic transducer passes through the coupling medium 103 and reaches the body 101. The coupling medium 103 may be composed of a material such as water whose ultrasonic absorption is small. The container 104 is for the purpose of preventing the flowing-out of the coupling medium 103. Here, the body 101 to be examined is a portion of a structure made up of a casting and contains a polycrystal portion of uneven quality. A portion of the ultrasonic pulse reaching the body 101 is propagated thereinto and scattered successively in response to variation of the acoustic quality therein. A portion of the scattered ultrasonic pulse goes reversely to the propagating path, i.e., the acoustic scan line, and returns back to the ultrasonic transducer 102 where it is converted into a reception signal. In steps of the propagation and the scattering, the ultrasonic pulse is affected by the acoustic quality of the body 101, i.e., the ultrasonic wave propagation characteristic and the ultrasonic wave scattering characteristic thereof. The reception signal is amplified in the receiving section 106 the output of which is detected by the detector 107 whose output is in turn stored and scan-transduced in the scan transducing section 108 the output of which is thus indicated at the indication section 109 may comprising a standard TV monitor or the like. On the other hand, the output of the receiving section 106 is processed for a signal analysis such as frequency analysis in the signal analysis section 110 so as to obtain the propagation characteristic and the scattering characteristic. The attenuation characteristic being one of the propagation characteristic may be obtained as follows. That is, initially derived are the reception signal h(R1) corresponding to a predetermined depth R1 within the body 101 and the reception signal h(R2) corresponding to a predetermined depth R2 therein. Here, the length of the derived signal is 5 mm within the body 101, for example. When the length of the derived signal is estimated to be 1 mm and the corresponding gate width is T microseconds, the relation can be expressed in accordance with the following relational equation.

$$T = 2 \cdot l/V \text{ where } V \text{ is the acoustic velocity (km/sec)} \quad (2)$$

Thus, as understood from this equation, it is required that the acoustic velocity V has been already known to determine the gate width. Data representing the acoustic velocity is required to be prepared in advance in accordance with materials. Secondly, a frequency analysis such as Fourier transformation is effected with respect to the reception signals h(R1) and h(R2). When the Fourier transformation of the reception signal h(R1) results in H1($\omega$) and the Fourier transformation of the reception signal h(R2) causes H2($\omega$) where $\omega$ represents an angular frequency, H1($\omega$) and H2($\omega$) can be expressed as follows.

$$H1(\omega) = T(\omega) \cdot G1(\omega) \cdot S1(\omega) \quad (3)$$

$$H2(\omega) = T(\omega) \cdot G2(\omega) \cdot S2(\omega) \quad (4)$$

where T($\omega$) represents the frequency characteristic of an ultrasonic wave pulse transmitted and received by the ultrasonic transducer 102, G1($\omega$) and G2($\omega$) respectively represents propagation characteristics in which the ultrasonic wave receives during the movement-back-and-forth thereof between the ultrasonic transducer 102 and the positions of the depths R1 and R2, and S1($\omega$) and S2($\omega$) are respectively scattering characteristics of the ultrasonic wave at the depths R1 and R2.

As obvious from these equations, the reception signal includes the ultrasonic propagation characteristic and the ultrasonic scattering characteristic in state of multiplication whereby difficulty is encountered to independently obtain them. However, if the scattering characteristics S1($\omega$) and S2($\omega$) are equal to each other, the propagation characteristic G21($\omega$) between the depths R1 and R2 within the body 101 can be obtained by taking the ratio of the equations (3) and (4). That is, $$\begin{aligned} G21(\omega) &= G2(\omega)/G1(\omega) \\ &= H2(\omega)/H1(\omega) \end{aligned} \quad (5)$$

Here, the absolute value of the propagation characteristic G21($\omega$) corresponds to the ultrasonic attenuation characteristic under the condition of no diffraction of the ultrasonic beam. Thus, the propagation characteristic of the ultrasonic wave can be obtained for predetermined regions within the body 101 to be examined, and the propagation characteristic G1($\omega$) between a surface of the body 101 and the position of the depth R1 can be also obtained and further the scattering characteristic S1($\omega$) can be obtained in accordance with the equation (3). However, in the case that the body 101 to be examined is composed of a scattering body of uneven quality, the ultrasonic scattering characteristic depends largely on the place and therefore it is impossible to estimate that S1($\omega$) and S2($\omega$) are equal to each other. On the other hand, contrary to this, utilized reversely is the fact that the ultrasonic scattering characteristic is varied at random in accordance with variation of the place to be examined. That is, the ultrasonic transducer 102 is moved in a predetermined range in directions parallel to the surface of the body 101 to obtain a number of reception signals from a number of places within the body 101, each of which is processed by the frequency analysis, and the results of the frequency analysis are averaged to cancel only the scattering characteristics varied at random. With respect to the averaged Fourier-transformation results H1($\omega$) and H2($\omega$), the equation (4) can be applied, thus allowing obtaining the propagation characteristic and so on.

In such an arrangement, the cancelling of the scattering characteristics can be made under the condition that the scattering characteristic of the ultrasonic wave within the body 101 is varied significantly at random when the place to be examined is changed, that is, the places to be examined are not in correlation to each other at all. However, a problem encountered in such an arrangement is that this condition cannot be satisfied when there includes boundary surfaces having a precise acoustic boundary, resulting in not allowing the cancelling thereof in this case. In addition, another problem in such an arrangement is to lengthen the measuring time period because of many times of transmissions and receptions of the ultrasonic wave.

SUMMARY OF THE INVENTION

The present invention has been developed in order to remove drawbacks inherent to the conventional apparatus.

It is therefore an object of the present invention to provide a new and improved ultrasonic examination apparatus which is capable of accurately measuring ultrasonic attenuation characteristics and the acoustic non-linear parameters in terms of a body to be examined which has various attenuation characteristics and acoustic velocity characteristics depending on tissues such as organism.

Another object of the present invention is to provide a new and improved ultrasonic examination apparatus which is capable of accurately measuring, for a shorter time, propagation characteristics of an ultrasonic wave such as ultrasonic absorption characteristic with respect to a body to be examined which has an arbitrary ultrasonic scattering characteristic.

According to a feature of the present invention, first and second ultrasonic pulse signals (pump wave pulse and probe wave pulse) whose frequencies are different from each other are transmitted into a body to be examined and the phase relation between the first and second ultrasonic wave is feedback-controlled so that the modulation characteristic of the reception signals based upon the non-linear effect assumes the maximum, thus obtaining acoustic characteristics such as ultrasonic attenuation characteristic and non-linear parameter on the basis of the modulation characteristic. The frequency of the probe wave pulse is higher than that of the pump wave pulse. Higher frequency wave propagates faster as compared with the lower frequency pulse due to dispersion relation of the sound speed in the frequency dependent attenuating medium. In this arrangement, the difference in velocity between the pump wave pulse and the probe wave pulse within the body to be examined is corrected, since this correction of the velocity difference allows superimposition of the probe wave pulse on the point at which the absolute value of the particle velocity or the absolute value of the particle acceleration of the pump wave pulse assumes the maximum at a portion to be examined, this permitting the measurement of acoustic characteristics such as non-linear parameter.

Another feature of the present invention is that two kinds of ultrasonic pulses whose frequencies are different from each other, i.e., first ultrasonic pulse and second ultrasonic pulse with a frequency higher than that of the first ultrasonic pulse, are transmitted into a body to be examined and the phase relation between the first and second ultrasonic pulses are controlled so that the modulation characteristic of the reception signal based on the amplitude dependence distortion assumes the maximum so as to obtain variation of the frequency characteristic of the reception signal of the second ultrasonic pulse in accordance with the modulation characteristic. The difference in velocity between the first and second ultrasonic pulses within the body is cancelled so that, at the place to be examined within the body, the second ultrasonic pulse can be superimposed upon the point at which the absolute value of the particle acceleration of the first ultrasonic pulse assumes the maximum, thereby making possible the measurement of the acoustic characteristics such as ultrasonic wave attenuation and scattering characteristic without receiving the influence of the ultrasonic scattering characteristic within the body.

A further feature of the present invention is that first and second ultrasonic pulses whose frequencies are different from each other are transmitted into a body to be examined and the phase relation between the first and second ultrasonic pulses is calculated so that the modulation characteristic of the reception signal based on the amplitude dependence distortion has a maximum, thus obtaining variation of the spectral distribution of the reception signal of the second ultrasonic pulse on the basis of the non-linear interaction between the first and second ultrasonic pulses in accordance with the modulation characteristic. The difference in velocity between the first and second ultrasonic pulses within the body to be examined is corrected so that, between two portions to be examined, the superimposition of the first and second ultrasonic pulses can be performed in the phase relation in which the modulation characteristic at the frequency region of the second ultrasonic pulse which is based upon the amplitude dependency distortion has a maximum, thereby allowing measurement of acoustic characteristics such as ultrasonic attenuation and scattering characteristic without being subjected to the influence of the ultrasonic scattering characteristic within the body to be examined.

Here, when the maximum beam width of the second ultrasonic pulse at the intersection of the first and second ultrasonic pulses is W, the angle made by the propagating direction of the first ultrasonic pulse and the propagating direction of the second ultrasonic pulse is $\theta$ and the wave length of the first ultrasonic wave is $\lambda$, it is desirable that ultrasonic transducers for generating the first and second ultrasonic pulses are arranged to be $\tan \theta \leq \lambda/2W$. Therefore, since it is possible to do that the phase relation of the second ultrasonic pulse with respect to the first ultrasonic pulse is not varied in space, the measurement of the non-linear parameter can be effected stably.

In accordance with the present invention, there is provided an ultrasonic examination apparatus comprising: ultrasonic transducing means for transmitting first and second ultrasonic pulses to a body to be examined, the frequency of said second ultrasonic pulse being higher than that of said first ultrasonic pulse; drive means for controlling the phases of said first and second ultrasonic pulses; and signal analysis means for controlling said drive means so that variation of a frequency characteristic of an ultrasonic reception signal of said second ultrasonic pulse assumes the maximum.

In accordance with the present invention, there is further provided an ultrasonic examination apparatus comprising: first ultrasonic transducing means for transmitting a first ultrasonic pulse into a body to be examined; second ultrasonic transducing means for transmitting a second ultrasonic pulse, whose frequency is higher than that of said first ultrasonic pulse, into said body; drive means for performing phase control so that the phase relation of said first and second ultrasonic pulses superimposed within said body is controlled to a desirable state; and signal analysis means for receiving reception signals of said second ultrasonic transducing means in response to driving said first and second ultrasonic transducing means plural times in different phase relations, estimating variation of the frequency characteristic on the basis of the reception signals and controlling said drive means so that the variation of the frequency characteristic assumes the maximum.

In accordance with the present invention, there is still further provided an ultrasonic examination apparatus comprising: first ultrasonic transducing means for transmitting a first ultrasonic pulse into a body to be examined; second ultrasonic transducing means for transmitting a second ultrasonic pulse, whose frequency is higher than that of said first ultrasonic pulse, into said body; drive means for performing phase control so that the phase relation of said first and second ultrasonic pulses superimposed within said body is controlled to a desirable state; and signal analysis means for receiving reception signals of said second ultrasonic transducing means in response to driving said first and second ultrasonic transducing means plural times in different phase relations, measuring variations of the frequency characteristic at first and second depths within said body on the basis of the reception signals, estimating variation of the difference of the frequency characteristics of said first and second depths, and controlling said drive means so that the variation of the frequency characteristic assumes the maximum.

BRIEF DESCRIPTION OF THE DRAWINGS

The object and features of the present invention will become more readily apparent from the following detailed description of the preferred embodiments taken in conjunction with the accompanying drawings in which:

FIGS. 2A, 2B and 2C are block diagrams showing an ultrasonic examination apparatus according to an embodiment of the present invention;

FIGS. 3A, 3B, 3C and 3D are illustrations for describing the waveforms of the outputs of first and second ultrasonic transducers;

FIGS. 4A, 4B and 4C are illustrations for describing distortion of ultrasonic waves due to the non-linear phenomenon of propagation;

FIGS. 8A and 8B are waveform diagrams for describing the output waveforms of ultrasonic transducers;

FIG. 9 is a block diagram showing an ultrasonic examination apparatus according to a further embodiment of the present invention;

DETAILED DESCRIPTION OF THE INVENTION

Figure 1:
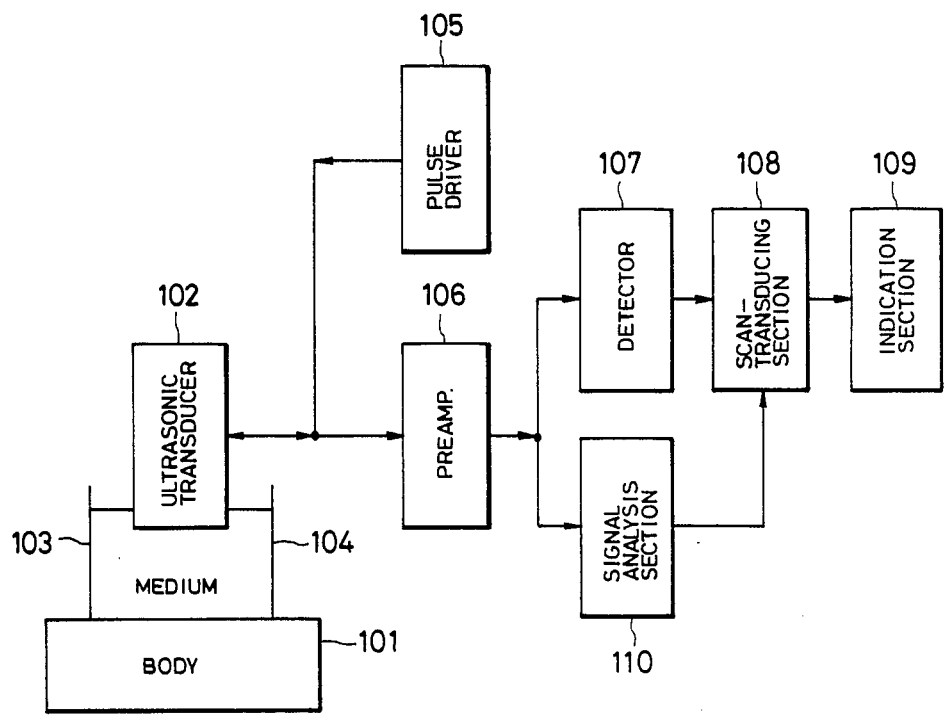
FIG. 1 is a block diagram showing a conventional non-destructive examination apparatus.
Figure 2A:
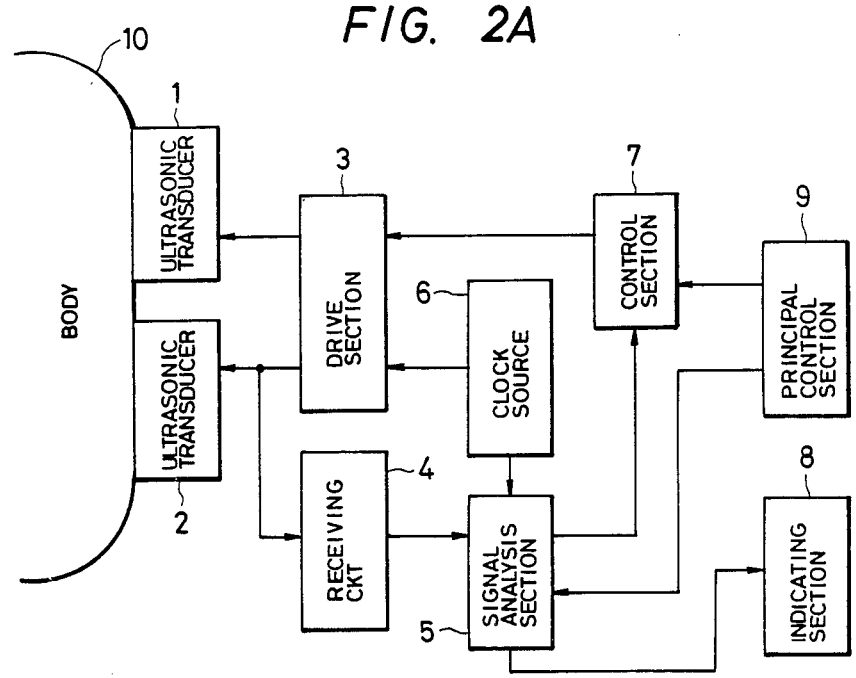
Figure 2B:
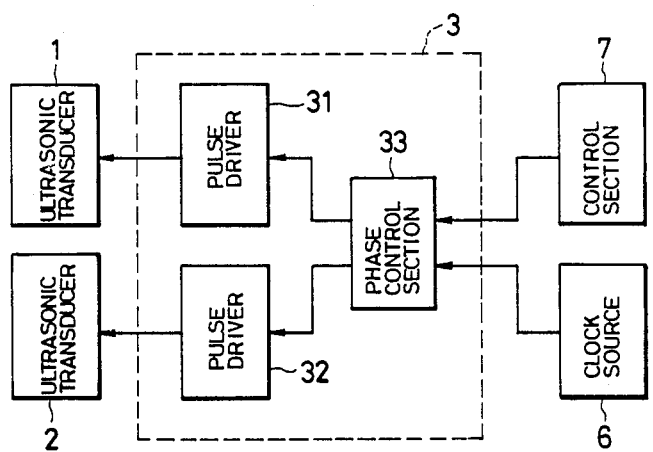

Referring now to FIGS. 2A to 2C, there is illustrated an ultrasonic examination apparatus according to a first embodiment of the present invention. In FIG. 2A, numeral 1 represents a first ultrasonic transducer for generating a first ultrasonic pulse of a low frequency band (pump wave pulse) and numeral 2 designates a second ultrasonic transducer for generating a second ultrasonic pulse (probe wave pulse) whose frequency is higher than that of the first ultrasonic pulse. The first and second ultrasonic transducers 1 and 2 are driven under phase control by means of a drive section 3 the detailed arrangement of which is illustrated in FIG. 2B. In FIG. 2B, the drive section 3 comprises a pulse driver 31 for driving the first ultrasonic transducer 1, a pulse driver 32 for driving the second ultrasonic transducer 2 and a phase control section 33 for controlling the timing difference of pulse generation between the pulse driver 31 and the pulse driver 32.

Returning back to FIG. 2A, numeral 4 is a receiving circuit for amplifying the reception output of the second ultrasonic transducer 2 and numeral 5 is a signal analysis section for performing a signal processing of the output of the receiving section 4, the detailed arrangement of the signal analysis section 5 being shown in FIG. 2C. In FIG. 2C, the signal analysis section 5 comprises an analog-to-digital (A/D) converter 51 for converting the output signal of the receiving section 4 into a digital signal, a memory 52 for storing the output of the A/D converter 51, a frequency analyzer 53 for performing the frequency analysis with respect to the output data of the memory 52, a calculation section 54 for detecting variation of the output of the frequency analyzer 53, and after-processing section for processing the output of the calculation section 54.

Return again to FIG. 2A, numeral 6 is a clock source for generating a clock signal and supplying it to the drive section 3 and so on and numeral 7 is a control section for feedback-controlling the drive section 3 on the basis of the output of the signal analysis section 5. Further provided therein are an indication section 8 for indicating the output of the signal analysis section 5 and a principal control section 9 for performing control of the entire apparatus. Numeral 10 is an object to be examined.

Operation of the ultrasonic examination apparatus of FIGS. 2A to 2C will be described hereinbelow with reference to FIG. 3 in which (a) shows one example of the second ultrasonic pulse (probe wave pulse) and (b) shows one example of the first ultrasonic pulse (pump wave pulse), and (c) and (d) are illustrations of the superimposition of the first and second ultrasonic pulses, these waveforms corresponding to the state variation of the drive section 3. The central frequency of the first ultrasonic pulse is 0.3 MHz, for example, and the central frequency of the second ultrasonic pulse is 3 MHz, for example, the values being set to be significantly different from each other. In FIG. 3(c), the center of gravity of the waveform of the second ultrasonic is superimposed at the timing that the particle velocity of the first ultrasonic pulse is in the vicinity of zero and the particle acceleration thereof shows the positive peak. This state is called phase state A. On the other hand, the case in which it is superimposed at the timing that the particle acceleration shows the negative peak is called phase state A'. In FIG. 3(d), the center of gravity of the waveform of the second ultrasonic pulse is superimposed at the timing that the particle velocity of the first ultrasonic pulse assumes the positive peak value, this state being called phase state B. On the other hand, the case in which it is superimposed at the timing of the negative peak value is called phase state B'. When the wave length of the first ultrasonic pulse is $\Lambda$ and the pulse length of the second ultrasonic pulse is t, it is desirable to be $$2t \leq \Lambda \qquad (6)$$

The satisfaction of the relation of the equation (6) causes easy analysis of the modulation characteristic of the second ultrasonic pulse.

The propagation of the respective pulses shown in FIG. 3 into the body 10 will be described in detail. It is known that, even in the case of the peak ultrasonic output level employed for general ultrasonic examination apparatus, the waveform of the ultrasonic wave is distorted due to the non-linear phenomenon of propagation, as described with the equation (1). The affection of this non-linear phenomenon of propagation to the waveform of the ultrasonic pulse is shown in FIG. 4, where (a) shows distortion of the first ultrasonic pulse due to the non-linear phenomenon and (b) and (c) show the modulation of the superimposed second ultrasonic pulse because of the distortion of the first ultrasonic pulse. In FIG. 4(b), the central frequency of the second ultrasonic pulse superimposed in the phase state A is shifted to the high-frequency side in accordance with the propagation, and in FIG. 4(c), the phase of the second ultrasonic pulse superimposed in the phase state B is shifted in accordance with the propagation. That is, these diagrams show variation of the propagation time. In the case that the second ultrasonic pulse is superimposed at the position slipped out by 180° with regard to the phase of the first ultrasonic pulse for the phase state A, the central frequency of the second ultrasonic pulse is lowered in accordance with the propagation. Thus, if taking the difference between the case of increase of the central frequency and the case of decrease thereof, it is rendered possible to obtain greatly the variation of the central frequency based upon the non-linear effect. Similarly, for the phase state B, it is rendered possible to greatly obtain the variation of the propagation time. The variation of the central frequency and the variation of the propagation time depend upon the magnitude of the first ultrasonic wave, non-linear parameter of the medium and ultrasonic attenuation characteristic. Therefore, it is possible to obtain the acoustic characteristic of the medium by measuring the variations of the central frequency and the propagation time.

Although in the above description the propagation velocities of the first and second ultrasonic pulses are equal to each other, actually, both the propagation velocities are not equal to each other because of two reasons. The first reason relates to dispersion of acoustic velocity in the frequency dependence attenuation medium, that is, although different in accordance with the kind of the tissue of the organism, when the ultrasonic frequency is different by one figure, the acoustic velocity of the high-frequency side is increased by about several to 10 m/sec as compared with that of the low-frequency side. The second reason is that, because the propagating directions of the first and second ultrasonic pulses are different from each other due to intercrossing thereof, the propagation velocities thereof are different from each other in appearance. As a result, it is difficult to keep the phase state A or the phase state B within the organism.

Subsequently, a description will be made hereinbelow in terms of steps in which a reception signal is obtained from the body in response to the respective ultrasonic waveforms of FIG. 3 in correspondence to the state variation of the drive section 3 and then processed. The ultrasonic transducer 2 is driven in response to operation of the pulse driver 32 of the drive section 3. The ultrasonic transducer 2 generates the second ultrasonic pulse (probe wave pulse) which is in turn propagated into the body 10 to be examined. At this time, the pulse driver 31 is not in operation so that the ultrasonic transducer 1 does not generate the first ultrasonic pulse (pump wave pulse). The second ultrasonic pulse propagating into the body 10 is scattered successively in accordance with the variation of the acoustic quality of the body 10 and the scattered ultrasonic wave is received by means of the ultrasonic transducer 2 and the reception signal is amplified in the receiving circuit 4 and then supplied to the signal analysis section 5. In the signal analysis section 5, the A/D converter 51 converts the output of the receiving circuit 4 into a digital signal. The sampling timing of the A/D converter 51 is controlled by the clock pulse of the clock source 6 and is in synchronism with the pulse drivers 31 and 32. The output data of the A/D converter 51 is stored in the memory 52. Of the data stored in the memory 52, the data of the window interval corresponding to the depth Z1 within the body 10 is processed by the frequency analysis in order to obtain a phase $\phi 1$. The length of the window interval is 1 cm, for example. Thereafter, the principal control section 9 supplies the control section 7 with delay data which is stored in advance under the condition that the phase state B can be realized in the depth Z1 within the body 10. The control section 7 then supplies this delay data to the drive section 3. The phase control portion 33 of the drive section 3 generates a delay pulse on the basis of the delay data and a clock from the clock source 6 and may be constructed of a preset-counter or the like. The pulse drivers 31 and 32 are operated with the time difference corresponding to the delay data in response to the delay pulse. The pulse driver 31 drives the ultrasonic transducer 1 which in turn generates the first ultrasonic pulse (pump wave pulse) to be propagated into the body 10. The first and second ultrasonic pulses intercrossed and superimposed within the body 10 to be examined are scattered due to the non-linear interaction and received by means of the ultrasonic transducer 2. The reception signal is amplified in the receiving circuit 4 and then supplied to the signal analysis section 5 after the frequency component corresponding to the first ultrasonic pulse (pump wave pulse) is removed by means of a band-pass filter or the like. In the signal analysis section 5, similarly, a phase $\phi 2$ is obtained on the basis of the data corresponding to the depth Z1. Subsequently, the control section 7 changes the delay data from the principal control section 9 and supplies the changed delay data to the drive section 3. For example, as the degree of the change is selected a value corresponding to the time of about 1/32 of one cycle of the first ultrasonic pulse. The phase of the reception signal obtained in accordance with the changed delay data is determined to be $\phi 3$. In the calculation section 54 are obtained the variation data of phase thus obtained, i.e., $\Delta\phi 2 = \phi 2 - \phi 1$, $\Delta\phi 3 = \phi 3 - \phi 1$ which are compared with each other to check the magnitudes of the phase variations. When $\Delta\phi 3$ is greater, the change of the delay data is continued in the control section 7. On the other hand, when $\Delta\phi 2$ is greater, the change of the delay data is made to the reverse direction. Thus, the phase variation $\Delta\phi 4 = \phi 4 - \phi 1$ corresponding to the changed data is obtained to perform comparison. The repetition of the above process allows determining the delay data by which the phase variation data assumes the maximum. The delay data is supplied to the drive section 3 whereby the state that the phase variation is maximum, i.e., phase state B, can be realized in the depth Z1 within the body 10 to be examined. In the above process for determining the delay data, the after-processing section 55 designates the changing amount of the delay data for the control section 7 on the basis of the phase variation data generated by the calculation section 54. On the basis of the delay data thus obtained, the control section 7 generates delay data corresponding to the phase states, B', A and A'. Here, the phase state B' can be also realized by reversing the polarity of the output pulse of the pulse driver 31. Furthermore, the phase state A' with respect to the phase state A can be similarly realized by reversing the polarity of the output pulse of the pulse driver 31.

Subsequently, a description will be made hereinbelow in terms of a process for obtaining the acoustic characteristic of the body 10 under the respective phase states of the body 10 realized thus. Here, the place to be examined within the body 10 is the interval between a depth point Z1 and a depth point Z2 which exists at a position deeper than Z1. Initially, the phase state A is realized at the depth Z1 to be examined and the phase state of the depth Z2 to be examined is similar to that of the depth Z1. In the signal analysis section 5, the frequency analysis is performed in terms of the data corresponding to the depths Z1 and Z2. The frequency analyzer 53 obtains a spectrum distribution in the case of the phase states A and A'. The spectral distribution corresponding to the depth Z1 on the phase state A is expressed as A(Z1), the spectral distribution corresponding to the depth Z2 thereon is expressed as A(Z2), the spectral distribution corresponding to the depth Z1 on the phase state A' is expressed as A'(Z1) and the spectral distribution corresponding to the depth Z2 thereon is expressed as A'(Z2). These spectral distributions can be expressed as follows using the spectral distribution T of the incidence probe wave pulse at each of the respective depths and the frequency characteristic S of the ultrasonic scattering.

$$A(Z1) = T(Z1) \cdot S(Z1) \quad (7)$$

$$A'(Z1) = T'(Z1) \cdot S(Z1) \quad (8)$$

$$A(Z2) = T(Z2) \cdot S(Z2) \quad (9)$$

$$A'(Z2) = T'(Z2) \cdot S(Z2) \quad (10)$$

Figure 5:
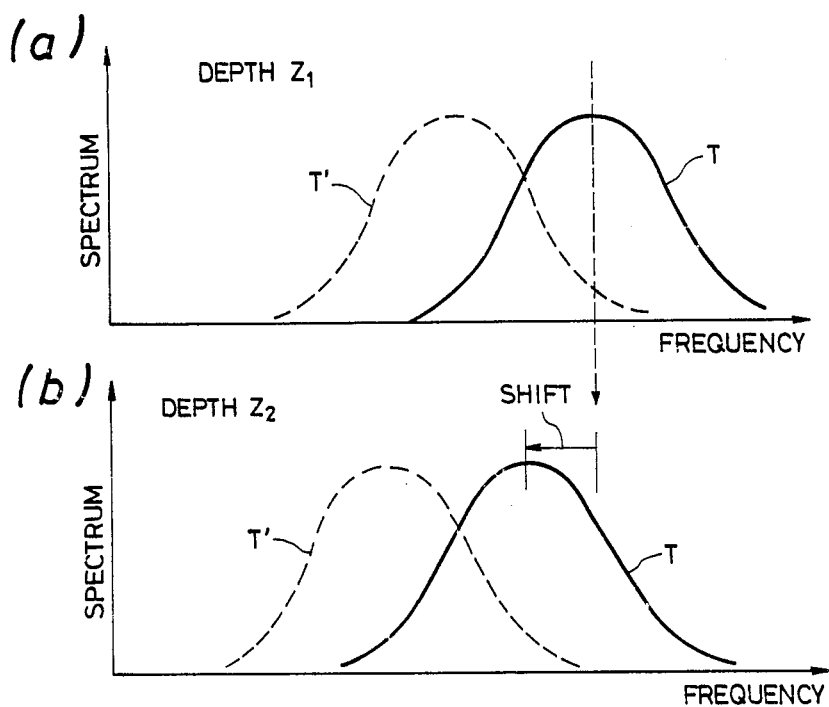
FIGS. 5A and 5B are illustrations for describing the spectral characteristic of an incidence probe wave pulse.

Here, the respective spectral characteristics of the incidence probe wave pulse are as shown in FIG. 5. That is, since the probe wave pulse is compressed in the phase state A, the spectral distribution T is shifted to the high-frequency side. On the other hand, in the phase state A', the spectral distribution T' of the probe wave pulse is shifted to the low-frequency side. Furthermore, due to the influence of the frequency dependence attenuation of the ultrasonic wave within the body 10, the spectral distribution T' on the depth Z2 is shifted to the low-frequency side as compared with the spectral distribution on the depth Z1. If it is allowed to measure the shift amount of the central frequency of the spectral distribution based on the ultrasonic attenuation, the ultrasonic attenuation characteristic of the body 10 can be obtained. However, the frequency dependency of the scattering characteristic S of the ultrasonic wave is very high, resulting in significantly great error. For elimination of the influence of the scattering characteristic S, the spectrum ratio R is obtained in terms of the equations (7) to (10) to cancel the scattering characteristic S. That is, $$R(Z1) = \frac{A(Z1)}{A'(Z1)} = \frac{T(Z1)}{T'(Z1)} \quad (11)$$

$$R(Z2) = \frac{A(Z2)}{A'(Z2)} = \frac{T(Z2)}{T'(Z2)} \quad (12)$$

Figure 6:
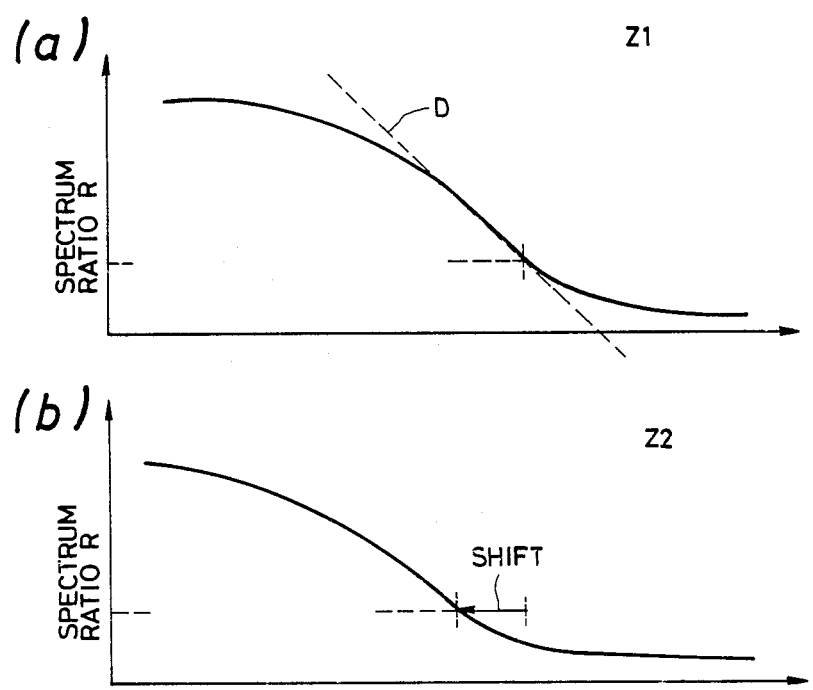
FIGS. 6A and 6B are illustrations for describing the spectrum ratio.

The spectrum ratios R(Z1) and R(Z2) are shown in FIG. 6. The shift amount of the spectrum ratio R corresponding to the depth on the frequency axis corresponds to the shift amount of the central frequencies of the spectral distributions T, T' with respect to the depth, and therefore, it is possible to obtain the ultrasonic wave attenuation characteristic within the body 10 from the shift amount of the spectrum ratio R. The calculation of the equations (11) and (12) and calculation of the spectrum ratio R are made in the calculation section 54. The after-processing section 55 obtains an attenuation factor on the basis of the shift amount of the spectrum ratio R obtained in the calculation section 54 and the obtained attenuation factor is indicated at the indication section 8. The attenuation factor may be obtained in accordance with the correspondence table of the shift amount of the spectrum ratio R and the attenuation factor which is prepared in advance. Although in the above description the phase state A is realized after the realization of the phase state B, it is considered to directly realize the phase state A. For example, the inclination D of the spectrum ratio R shown in FIG. 6(a), i.e., variation data, is a value corresponding to the shift of the central frequency of the probe wave pulse based upon the non-linear effect on the phase states A and A', and therefore, it can be realized by controlling the control section 3 so that the inclination D, i.e., variation data, assumes the maximum.

As obvious from the above description, according to this embodiment, it is possible to realize the phase states such as A and B within the body 10 such as organism having complex acoustic velocity characteristic by means of the control section 7, and further it is possible to measure the ultrasonic attenuation characteristic without being subjected to the influence of the ultrasonic scattering characteristic within the body 10 with the shift amount of the spectrum ratio R on the frequency axis. Although in the above-mentioned embodiment the ultrasonic attenuation is obtained, since the phase variation of the reception signal in the phase state B is a value determined on the basis of the sound pressure of the pump wave pulse and the acoustic non-linear parameter B/A, if the information relating to the sound pressure of the pump wave pulse within the body 10 is stored in advance in the after-processing section 15 or the like, it is possible to obtain the value of the non-linear parameter B/A.

As described above, in this embodiment, the control section accurately controls the phase state of superimposition of the probe wave pulse and the pump wave pulse within a body to be examined, thereby measuring the acoustic parameter B/A and ultrasonic attenuation characteristic using the non-linear interaction between these pulses. Therefore, it is possible to accurately control the phase state of superimposition of the probe wave pulse and the pump wave pulse within the body such as organism having complex acoustic velocity characteristic and to accurately measure the acoustic characteristic, resulting in a great effect.

Figure 7:
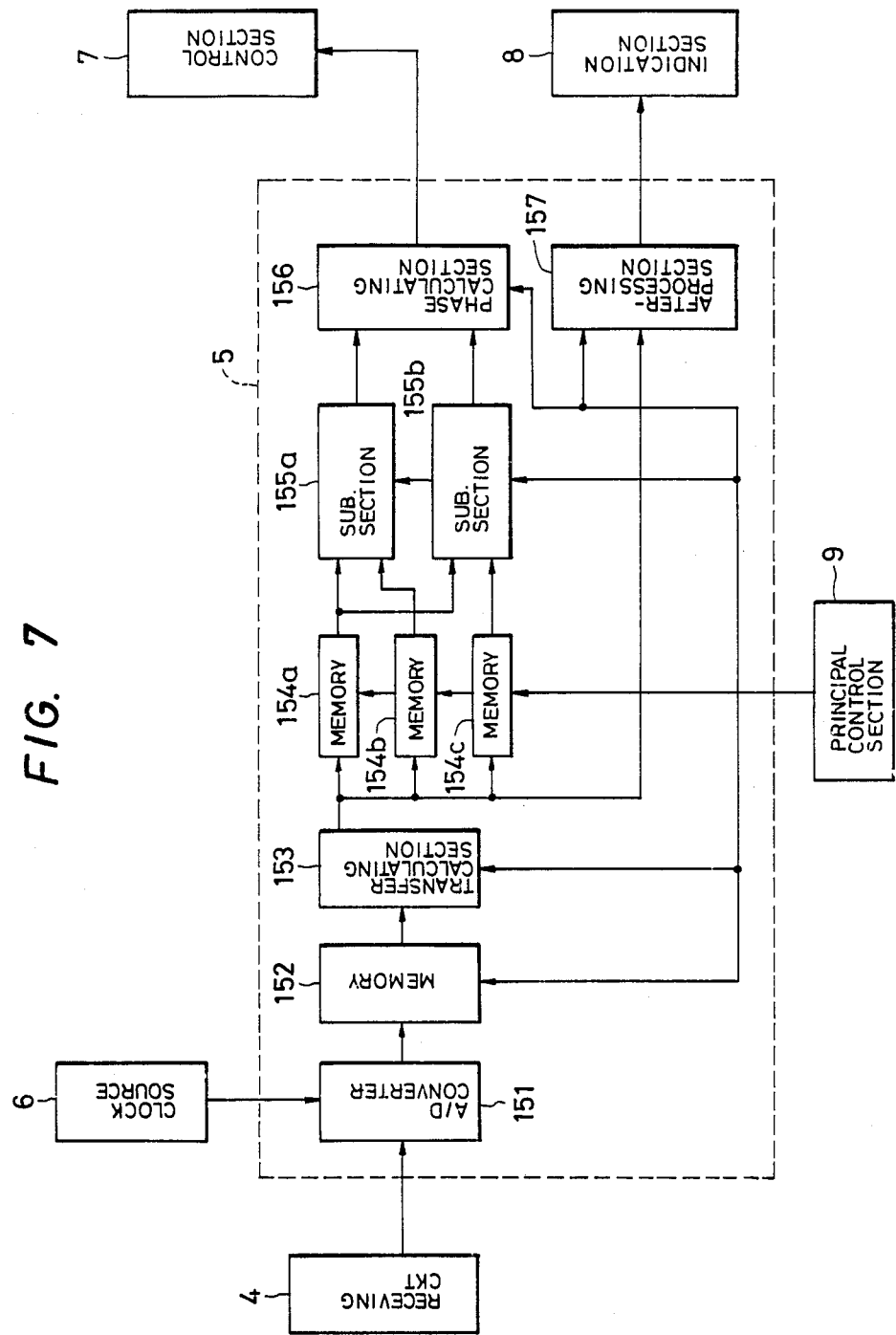
FIG. 7 is a block diagram showing an ultrasonic examination apparatus according to another embodiment of the present invention.

A second embodiment of the present invention is similar in the basic arrangement to the first embodiment of FIG. 2A to 2C and the difference therebetween is characterized by an arrangement of the signal analysis section 5 which is shown in FIG. 7. The second embodiment will be described hereinbelow with reference to FIG. 2A and FIG. 2B and FIG. 7. In FIG. 7, illustrated at numeral 151 is an analog-to-digital (A/D) converter which is coupled to a receiving circuit 4 for converting the output signal of the receiving circuit 4 into a digital signal and illustrated at numeral 152 is a memory coupled to the A/D converter 151 for storing the output of the A/D converter 151. Numeral 153 is a transfer characteristic calculating section for performing the frequency analysis with respect to the output data of the memory 152 and numerals 154a, 154b, 154c are respectively memories coupled to the transfer characteristic calculating section 153 for respectively storing the output data thereof. The memories 154a and 154b are coupled to a subtraction section 155a and the memories 154a and 154c are coupled to another subtraction section 155b. The subtraction sections 155a and 155b are connected to a phase calculation section 156. Numeral 157 represents an after-processing section coupled to the transfer characteristic calculating section 153. Namely, the signal analysis section 5 comprises the A/D converter 151, memory 152, transfer characteristic calculating section 153, memories 154a to 154c, subtraction sections 155a, 155b, phase calculating section 156 and after-processing section 157. The signal analysis section 5, as shown in FIGS. 2A, 2B and FIG. 7, coupled to a clock source 6 for supplying a clock to a drive section 3 and so on, a control section 7 for controlling the drive section 3 in accordance with the output of the signal analysis 5, an indication section 8 for indicating the output of the signal analysis section 5 and a principal control section 9 for performing control of the entire apparatus.

Operation of the above-mentioned arrangement will be described hereinbelow. One example of the first ultrasonic pulse is shown in (a) of FIG. 8 and one example of the second ultrasonic pulse is shown in (b) of FIG. 8. These waveforms correspond to the state variation of the drive section 3. The central frequency of the first ultrasonic pulse is 0.5 MHz, for example, and the central frequency of the second ultrasonic pulse is 7.5 MHz, for example. That is, both the central frequencies are significantly different from each other. When the wave length of the first ultrasonic pulse is $\Lambda$ and the wave length of the second ultrasonic pulse is t, it is also desirable to be $2t < \Lambda$ (6). When the relation of the equation (6) is satisfied, the analysis of the modulation characteristic of the second ultrasonic pulse becomes easy. When the center of gravity of the second ultrasonic pulse shown in (b) of FIG. 8 is superimposed on a portion of the first ultrasonic pulse at which the sound pressure variation is a positive peak, this state is called phase state A. When it is superimposed on a portion thereof at which the sound pressure variation is negative peak, this state is called phase state B. A description will be made in terms of the modulation characteristic.

It is generally known that, even in the case of a peak ultrasonic output level employed for general ultrasonic examination apparatus, the waveform of the ultrasonic wave is distorted due to the amplitude dependence distortion of propagation. That is, the cause can be easily explained from the following equation (13).

$$V = Vo + \beta \Delta p / poVo \quad (13)$$

where $\Delta p$ is a sound pressure variation, $\beta$ is an amplitude dependence distortion constant, Vo represents the acoustic velocity of an ultrasonic wave of infinite small-amplitude, Po is the density at static pressure, and V is an acoustic velocity changed by the amplitude dependence distortion. In the equation (13), when the sign of the sound pressure variation $\Delta p$ is positive, the acoustic velocity variation is increased. When negative, it is decreased. This means that the waveform of the acoustic wave is finally distorted. In the affection of the amplitude dependence distortion phenomenon of propagation to the waveform of the ultrasonic pulse, when the superimposition is made with the phase state A, the central frequency of the second ultrasonic pulse is varied to the high-frequency side in accordance with the propagation. On the other hand, with the phase state B, the central frequency of the second ultrasonic pulse is decreased in accordance with the propagation. Therefore, if taking the difference between the case of increase of the central frequency and the case of decrease thereof, it is possible to greatly obtain the variation amount of the central frequency based upon the influence of the amplitude dependence distortion. The variation of these central frequencies depend upon the magnitude of the first ultrasonic pulse, the amplitude dependence distortion constant $\beta$ of the medium and the ultrasonic attenuation characteristic. Thus, it is possible to obtain the acoustic characteristic of the medium by measuring the variation of these central frequencies. Although in the above description the propagating velocities of the first and second ultrasonic pulses are equal to each other, actually these propagating velocities are not equal to each other. The first reason relates to dispersion of acoustic velocity in the frequency dependence attenuation medium, that is, although different in accordance with the kind of the tissue of the organism, when the ultrasonic frequency is different by one figure, the acoustic velocity of the high-frequency side is increased by about several to 10 m/sec as compared with that of the low-frequency side. The second reason is that, because the propagating directions of the first and second ultrasonic pulses are different from each other due to intercrossing thereof, the propagation velocities thereof are different from each other in appearance. As a result, it is difficult to keep the phase state A or the phase state B within the body 10 to be examined.

Subsequently, a description will be made in terms of steps of obtaining the reception signal from the body in response to the ultrasonic pulse waveform corresponding to the state variation of the drive section 3 and of processing it. The ultrasonic transducer 2 is initially driven in response to operation of the pulse driver 32 of the drive section 3 shown in FIG. 2B. The ultrasonic transducer 2 generates the second ultrasonic pulse which is in turn propagated into the body 10. At this time, the ultrasonic transducer 1 is not in operation so that the first ultrasonic pulse is not generated. The second ultrasonic pulse propagating into the body 10 is successively scattered in accordance with variation of the acoustic quality within the body 10 and the scattered ultrasonic wave is received by means of the ultrasonic transducer 2 and the reception signal is supplied to the signal analysis section 5 after amplified in the receiving circuit 4 of FIG. 2A. In the signal analysis 5, as shown in FIG. 7, the sampling timing of the A/D converter 151 is controlled by a clock pulse from the clock source 6. This sampling timing is same as the pulse drivers 31 and 32. The output data of the A/D converter 51 is stored in the memory 152. Of the data stored in the memory 152, the data at the window interval corresponding to the length of about 1 cm (for example) at a portion corresponding to the depth Z1 within the body 10 is processed in the transfer characteristic calculating section 153 for the frequency analysis so as to obtain a phase $\phi s(Z1, \omega)$ which is in turn stored in the memory 154a, where $\omega$ is an angular frequency. The principal control section supplies the control section 7 with delay data which is stored in advance. Here, the phase state of the first and second ultrasonic pulses superimposed within the body 10 is a phase state C. The control section 7 supplies this delay data to the drive section 3. The phase control section 33 of the drive section 3 generates a delay pulse on the basis of the delay data and a clock generated from the clock source 6. The phase control section 33 may be constructed of a preset counter or the like. The pulse driver 31 and 32 are operated in response to the delay pulse with the time difference corresponding to the delay data. The pulse driver 31 drives the ultrasonic transducer 1 to generate the first ultrasonic pulse and the pulse driver 32 drives the second ultrasonic transducer 2 to generate the second ultrasonic pulse, so that the first and second ultrasonic pulses are propagated into the body 10. The phase state of the first and second ultrasonic pulses intercrossed and superimposed within the body 10 is varied as described above. For example, for realizing the phase state A at the depth Z1 within the body 10, even if the control section 7 outputs the delay data corresponding to the phase state A, the phase state of the reception signal corresponding to the actual depth Z1 is different from the phase state A. The first and second ultrasonic pulses intercrossed and superimposed within the body 10 are subjected to influence of the scattering and amplitude dependence distortion and received by means of the ultrasonic transducer 2. The reception signal is amplified in the receiving section 4 and supplied to the signal analysis section 5 after the frequency component corresponding to the first ultrasinic pulse is removed by means of a band-pass filter or the like. In the signal analysis section 5, as well as in the above-mentioned case of no first ultrasonic pulse, a phase $\phi 1(Z1, \omega)$ is obtained with respect to the data corresponding to the depth Z1 and stored in the memory 154b. Thereafter, the control section 7 changes the delay data of the phase state C supplied from the principal control section 9 to supply the changed delay data to the drive section 3. The changed delay data is used for shifting the position of the second ultrasonic pulse superimposed on the first ultrasonic pulse with respect to the phase state C. For example, this shifting is made by 90° in the phase of the first ultrasonic pulse with respect to the phase relation of the second ultrasonic pulse on the first ultrasonic pulse in the phase state C. This state is called phase state D. With the phase state D, the first and second ultrasonic pulses are propagated into the body 10 and scattered therein and received by means of the ultrasonic transducer 2. This reception signal is frequency-analyzed in the signal analysis section 5 as well as in the case of the phase state C to obtain phase $\phi 2(Z1, \omega)$ about the data corresponding to the depth Z1, the obtained phase being stored in the memory 154c. Here, for example, the phase $\phi 1 (Z1, \omega)$ stored in the memory 154 b is the phase at the depth Z1 within the body 10 and this phase is the sum of the phase obtained when only the second ultrasonic pulse is propagated and the phase varied due to the influence of the amplitude dependence distortion when the first and second ultrasonic pulses are superimposed at the phase state B. Here, the phase varied due to the amplitude dependence distortion may be obtained by subtracting the phase $\phi s(Z1, \omega)$, i.e., the phase of the depth Z1 in the case that only the second ultrasonic pulse is propagated, from the phase $\phi 1(Z1, \omega)$. That is, when the phase varied due to the influence of the amplitude dependence distortion in the phase state C is $\phi 1s(Z1, \omega)$ at the depth Z1 and the phase of the depth Z1 in the phase state D is $2s(Z1, \omega)$, the calculation can be made in accordance with the following equations (14).

$$\phi s(Z1, \omega) = \phi 1(Z1, \omega) - \phi s(Z1, \omega)$$

$$\phi 2s(Z1, \omega) = \phi 2(Z1, \omega) - \phi s(Z1, \omega) \quad (14)$$

The calculations of the equation (14) are made in the subtraction sections 155a and 155b, respectively. The phase calculating section 156 calculates the delay data using $\phi 1s(Z1, \omega)$ and $\phi 2s(Z1, \omega)$, which is the outputs of the subtraction sections 155a and 155b, so that the phase variation results in the maximum. That is, the delay data is determined to take the phase state A and the phase state B at the depth Z1. This process will be described hereinbelow. A phase of a given frequency such as the central frequency fo of the ultrasonic transducer 2 is obtained on the basis of $\phi 1s(Z1, \omega)$ and $\phi 2s(Z1, \omega)$, thus obtaining $\phi 1s(Z1, fo)$ and $\phi 2s(Z1, fo)$ which are respectively a value in the phase state C and a value in the phase state D in which the phase is shifted by 90° in the phase relation of the first and second ultrasonic pulses. It is assumed that these phases follow an relational equation (15).

$$y = L \sin(x + \theta) \quad (15)$$

In the case of the phase state C, $x = 0$ and in the case of the phase state D, $x = 90°$. Thus, $\theta$ and L can be obtained in accordance with the following equations (16).

$$\theta = TAN^{-1}(\phi 1s(Z1, fo)/\phi 2s(Z1, fo))$$

$$L = \phi 1s(Z1, fo)/\sin(\theta) \quad (16)$$

The phase calculating section 56 can calculate, using $\theta$ and L, the delay data for the phase states A and B with the reception signal corresponding to the depth Z1 because the phase state C is made when $X = 0$ in the equation (15). The phase state B can be realized by reversing the polarity of the output pulse of the pulse driver 31 with respect to the case of the phase state A.

Subsequently, a description will be made in terms of the process of obtaining the acoustic characteristic of the body 10 on the basis of the respective phase states realized thus. The portion to be examined is the interval between a depth Z1 and a depth Z2 deeper than Z1. Initially, the phase state A is realized at the depth Z1. Similarly, the phase state A is realized with respect to the depth Z2 as well as the case of the depth Z1. That is, the distance between the depths Z1 and Z2 is determined so that the phase state is not varied greatly. In the signal analysis 5, the frequency analysis is effected for the data corresponding to the depths Z1 and Z2 to be examined. The transfer characteristic calculating section 153 obtains the frequency characteristic of the reception signal in the case of the phase states A and B. The frequency characteristic of the reception signal corresponding to the depth Z1 in the phase state A is expressed as A(Z1), the frequency characteristic of the reception signal corresponding to the depth Z2 is expressed with A(Z2), the frequency characteristic of the reception signal corresponding to the depth Z1 in the phase state B is expressed by B(Z1), and the frequency characteristic of the reception signal corresponding to the depth Z2 is expressed with B(Z2). These frequency characteristics can be expressed as follows using the frequency characteristic S of ultrasonic scattering, propagation characteristic G and the transmission frequency characteristic T of the second ultrasonic pulse on the respective depths to be examined.

$$A(Z1) = T^A(Z1) \cdot S(Z1) \cdot G(Z1) \quad (17)$$

$$B(Z1) = T^B(Z1) \cdot S(Z1) \cdot G(Z1) \quad (18)$$

$$A(Z2) = T^A(Z2) \cdot S(Z2) \cdot G(Z2) \quad (19)$$

$$B(Z2) = T^B(Z2) \cdot S(Z2) \cdot G(Z2) \quad (20)$$

In the phase state A, the second ultrasonic pulse is compressed and hence the frequency characteristic $T^A$ is varied to the high-frequency side, and in the phase state B, the frequency characteristic $T^B$ of the second ultrasonic pulse is vaired to the low-frequency side. Furthermore, the spectral distributions $T^A$, $T^B$ on the depth Z2 is varied to the low-frequency side as compared with the frequency characteristic of the reception signal on the depth Z1, because of the influence of the frequency dependence attenuation of the ultrasonic wave within the body 10. To measure the variation amount of the central frequency of the frequency characteristic due to this ultrasonic wave attenuation can result in the ultrasonic attenuation characteristic of the body 10 to be examined. However, the frequency dependency of the scattering characteristic S of the ultrasonic is extremely great, and therefore this method causes a significantly great error. For eliminating the influence of this scattering characteristic S, with respect to the equations (17) to (20), the frequency characteristic ratio R is obtained and the scattering characteristic S is removed. That is, $$R(Z1) = \frac{A(Z1)}{B(Z1)} = \frac{T^A(Z1)}{T^B(Z1)} \quad (21)$$

$$R(Z2) = \frac{A(Z2)}{B(Z2)} = \frac{T^A(Z2)}{T^B(Z2)} \quad (22)$$

Since the variation amounts of the frequency characteristic ratios R(Z1), R(Z2) corresponding to the depth on the frequency axis correspond to the variation amounts of the central frequencies of the frequency characteristics $T^A$, $T^B$ corresponding to the depth, it is possible to obtain the attenuation characteristic of the ultrasonic within the body 10 on the basis of the variation amounts of the frequency characteristic ratios. The calculations of the equations (21) and (22) are performed in the after-processing section 57 and further the attenuation factor is obtained on the basis of the variation amounts of the frequency characteristic ratios R and indicated on the indication section 8. The attenuation factor may be obtained from a corresponding table for the variation amount of the frequency characteristic ratio and the attenuation factor which is prepared in advance.

As understood from the above description, according to this embodiment, measured initially on the depth Z1 to be examined are the phase of only the second ultrasonic pulse, the phase when the first and second ultrasonic pulses are superimposed at a given phase state, the phase in the case of superimposition at the phase state slipped out by 90° (for example) therefrom, whereby it is possible that the first and second ultrasonic pulses are superimposed at a predetermined phase state, for example, phase state A, B. Further, it is possible to accurately measure the ultrasonic attenuation characteristic without being subjected to the influence of the ultrasonic scattering characteristic of the body with the maximum variation amount of the frequency characteristic ratio R due to the influence of the amplitude dependence distortion on the frequency axis being obtained.

Although in this embodiment, for obtaining $\theta$ and L in the equation (15), the phase on the depth Z1 under the condition of no first ultrasonic pulse is subtracted to obtain the phase variation amount based on the influence of the amplitude dependence distortion, it is also appropriate that the following equation (23) may be used instead of the equation (15) and L, $\theta$, M in the equation (23) are obtained from the phase obtained when the first and second ultrasonic pulses are superimposed in a plurality of phase states.

$$y = L \sin(x + \theta) + M \quad (23)$$

As described above, in this embodiment, the signal analysis section accurately controls the phase state of superimposition of the first and second ultrasonic pulses within the body and measures the ultrasonic attenuation characteristic and so on of the body using the influence of the amplitude dependence distortion of these two pulses. Therefore, it is possible to accurately control the phase state of the first and second ultrasonic pulses within the body having a complex acoustic velocity characteristic and to accurately measure the acoustic characteristic, resulting a great effect. This embodiment can be also employed for the examination of tissues of an edible meat.

A third embodiment of the present invention will be further described hereinbelow. A feature of this third embodiment with respect to the first or second embodiment is the signal analysis section 5 and the basic arrangement thereof is similar thereto. Thus, the description thereof will be made with reference to FIG. 9 and FIGS. 2A and 2B. In FIG. 9, numeral 251 is an A/D converter coupled to the receiving circuit 4 for converting the output signal thereof into a digital signal, numeral 252 represents a memory coupled to the A/D converter 251 for storing the output of the A/D converter 251, numeral 253 designates a transfer characteristic calculating section for performing the frequency analysis with respect to the output data of the memory 252. The transfer characteristic calculating section 253 is coupled to memories 254a to 254f which respectively store the output data of the transfer characteristic calculating section 253. The memories 254a and 254b are respectively coupled to a subtraction section 255a, the memories 254a and 254c are respectively connected to a subtraction section 255b, the memories 254d and 254e are respectively coupled to a subtraction section 255c, and the memories 254d and 254f are respectively coupled to a subtraction section 255d. The subtraction sections 255a to 255d are in turn coupled to a phase calculating section 256. Numeral 257 is an after-processing section coupled to the transfer characteristic calculating section 253 and so on.

Operation will be principally described hereinbelow in terms of the signal analysis section 5, because the operation of the sections other than the signal analysis section 5 is similar to that of the previously described embodiment.

A reception signal amplified in the receiving circuit 4 is supplied to the signal analysis section 5 in which the sampling timing of the A/D converter 251 is controlled by a clock pulse from the clock source 6. This sampling timing is synchronized with the pulse drivers 31 and 32. The output data of the A/D converter 251 is stored in the memory 252. Of the reception signals stored in the memory 252, the reception signal at the window interval corresponding to about 1 cm (for example) at a portion corresponding to the depth Z1 within the body 10 to be examined are frequency-analyzed in the transfer characteristic calculating section 253 to obtain a phase $\phi s(Z1, \omega)$ which in turn stored in the memory 254a where $\omega$ is an angular frequency. Thereafter, the frequency analyzer 253 similarly performs the frequency analysis the reception signal of the stored reception signals corresponding to the depth Z2 deeper than Z1 within the body 10, with respect to a window interval of about 1 cm, to obtain a phase $\phi s(Z2, \omega)$, which is in turn stored in the memory 254d. The principal control section 9 then supplies the control section 7 with delay data D1 which is stored in advance. At this time, the phase relation of the first ultrasonic pulse with respect to the second ultrasonic pulse superimposed within the body 10 is C. The control section 7 sends this delay data D1 to the drive section 3. The phase control section 33 of the drive section 3 generates a delay pulse on the basis of this delay data D1 and a clock from the clock source 6. The phase control section 33 may be constructed of a preset counter or the like. The pulse drivers 31 and 32 are operated with the time difference corresponding to the delay data in response to the delay pulse. The pulse driver 31 drives the ultrasonic transducer 1 to generate a first ultrasonic pulse and the pulse driver 32 drives the ultrasonic transducer 2 to generate a second ultrasonic pulse. The two ultrasonic pulses are propagated through the coupling medium 11 into the body 10 to be examined. The phase relation of the first and second ultrasonic pulses intercrossed and superimposed within the body 10 is varied in accordance with the propagation distance as described above. For example, even if the control section 7 generates the delay data corresponding to the phase state A for realizing the phase relation A at the depth Z1 within the body 10, the actual phase relation at the portion corresponding to the depth Z1 is different from the phase relation A. The first and second ultrasonic pulses intercrossed and superimposed within the body 10 are subjected to the influence of scattering and amplitude dependence distortion and then received by the ultrasonic transducer 2. The reception signal is amplified in the receiving section 4 and supplied to the signal analysis section 5 after the frequency component corresponding to the first ultrasonic pulse is removed by means of a band-pass filter or the like. In the signal analysis section 5, as well as in the case of no supply of the first ultrasonic pulse, a phase $\phi 1(Z1, \omega)$ is obtained for the reception signal corresponding to the depth Z1 and a phase $\phi 1(Z2, \omega)$ is also obtained for the reception signal corresponding to the depth Z2 and both are stored in the memories 254b and 254e. Subsequently, the control section 7 changes the delay data D1 from the principal control section 9 and supplies the changed delay data D2 to the drive section 3. The changed delay data D2 corresponds to a phase shifted by 90° with respect to the phase state C. This phase relation is called phase relation D. With this phase relation D, the first and second ultrasonic pulses are propagated into the body 10 to be examined and scattered therewithin and received by means of the ultrasonic transducer 2. This reception signal is frequency-analyzed in the signal analysis section 5 as well as the case of the phase relation C to obtain a phase $\phi 2(Z1, \omega)$ for the reception signals corresponding to the depth Z1 and to obtain a phase $\phi 2(Z2, \omega)$ for the reception signal corresponding to the depth Z2, these obtained phases being stored in the memories 254c and 254f, respectively. Here, the phase $\phi 1(Z1, \omega)$ in the memory 254b corresponds to the depth Z1 within the body 10 and this corresponds to a combination of the phase in the case of propagating only the second ultrasonic pulse thereinto and the phase varied due to the amplitude dependence distortion in the case of superimposition of the first and second ultrasonic pulses in the phase relation C. The phase varied due to the amplitude dependence distortion can be obtained by subtracting the phase of the depth Z1 in the case of only the second ultrasonic pulse, i.e., the phase $\phi(Z1, \omega)$, from the phase $\phi 1(Z, \omega)$. When the phase variation amount of the depth Z1 due to the amplitude dependence distortion in the phase relation C is $\phi 1s(Z1, \omega)$, the phase variation amount of the depth Z2 is $\phi 1s(Z2, \omega)$ and the phase variations in the case of the phase relation D are respectively $\phi 2s(Z1, \omega)$ and $\phi 2s(Z2, \omega)$, these can be obtained in accordance with the following equation (24).

$$\phi 1s(Z1, \omega) = \phi 1(Z1, \omega) - \phi s(Z1, \omega)$$

$$\phi 1s(Z2, \omega) = \phi 1(Z2, \omega) - \phi s(Z2, \omega)$$

$$\phi 2s(Z1, \omega) = \phi 2(Z1, \omega) - \phi s(Z1, \omega)$$

$$\phi 2s(Z2, \omega) = \phi 2(Z2, \omega) - \phi s(Z2, \omega) \quad (24)$$

These calculations of the equation (24) are performed in the subtraction sections 255a to 255d, respectively. The information relating to the phases obtained here are of ten kinds which are indicated in the following table 1.

TABLE 1

| NAME | CONTENT |
|---|---|
| $\phi s(Z1, \omega)$ | phase of depth Z1 in the case of no first ultrasonic pulse |
| $\phi s(Z2, \omega)$ | phase of depth Z2 in the case of no first ultrasonic pulse |
| $\phi 1(Z1, \omega)$ | phase of depth Z1 in phase state C |
| $\phi 1(Z2, \omega)$ | phase of depth Z2 in phase state C |
| $\phi 2(Z1, \omega)$ | phase of depth Z1 in phase state D |
| $\phi 2(Z2, \omega)$ | phase of depth Z2 in phase state D |
| $\phi 1s(Z1, \omega)$ | phase variation of depth Z1 in phase state C |
| $\phi 1s(Z2, \omega)$ | phase variation of depth Z2 in phase state C |
| $\phi 2s(Z1, \omega)$ | phase variation of depth Z1 in phase state D |
| $\phi 2s(Z2, \omega)$ | phase variation of depth Z2 in phase state D |

Subsequently, a description will be made in terms of a method of producing the delay data for the first and second ultrasonic pulses, which is necessary for realizing the maximum phase variation between the depth Z1 and the depth Z2, using the four phase variation amounts $\phi 1s(Z1, \omega)$, $\phi 1s(Z2, \omega)$, $\phi 2s(Z1, \omega)$, $\phi 2s(Z2, \omega)$ obtained in accordance with the equation (24). The outputs of the subtraction sections 155a to 255d are transferred to the phase calculating section 256 where the following calculation will be performed. The phase variation amounts at a given frequency of the depths Z1, Z2 in the phase relation C., such as the central frequency $\omega o$ of the transmitted second ultrasonic pulse, is derived from $\phi 1s(Z1, \omega)$, $\phi 1s(Z2, \omega)$. The results are respectively expressed as $\phi 1s(Z1, \omega o)$ and $\phi 1s(Z2, \omega o)$. Similarly, the phase variation amounts of the depths Z1 and Z2 in the phase relation D are respectively expressed as $\phi 2s(Z1, \omega o)$ and $\phi s(Z2, \omega o)$. The differences are calculated using the four phase variation amounts in accordance with the following equation (25).

$$\Delta\phi 1s = \phi 1s(Z1, \omega o) - \phi 1s(Z2, \omega o)$$
$$\Delta\phi 2s = \phi 2s(Z1, \omega o) - \phi 2s(Z2, \omega o) \quad (25)$$

where $\Delta\phi 1s$ the difference between the phase variation amounts of the depths Z1 and Z2 in the phase relation C, and $\Delta\phi 2s$ is the difference between the phase variation amounts of the depths Z1 and Z2 in the phase relation D that the phase is shifted by 90° with respect to the phase relation C. If $\Delta\phi 1s$ and $\Delta\phi 2s$ are varied in sine-wave form, the phase can be expressed by the following equation (26).

$$y = A \sin(x + \theta) \quad (26)$$

In the equation (26), $\Delta\phi 1s$ is substituted when $x=0$ and $\Delta\phi 2s$ is substituted when $x=90°$, resulting in the following equation (27).

$$\Delta\phi 2s = A \sin(\theta)$$

$$\Delta\phi 2s = A \sin(90° + \theta) \quad (27)$$

Thus, $\theta$ and A can be respectively obtained as follows.

$$\theta = TAN^{-1}(\Delta\phi 1s/\Delta\phi 2s)$$

$$A = \Delta\phi 1s/(\sin(\theta)) \quad (28)$$

$\theta$ and A are calculated in the phase calculating section 256 on the basis of the four outputs of the subtraction sections 255a to 255d. Correction is performed using $\theta$ obtained thus to allow realization of the phase relations A and B between the depths Z1 and Z2 within the body 10. That is, in the phase relations A and B, the result of the equation (26) becomes zero. Therefore, the phase z of the first ultrasonic pulse with respect to the second ultrasonic pulse are as follows.

$$z = -\theta$$

$$z = 180° - \theta \quad (29)$$

The delay data corresponding to the respective phases Z are obtained in the principal control section 9 and supplied to the control section 7, thereby actually realizing the phase relation A and the phase relation B.

Secondly, a description will be made hereinbelow in terms of a process of obtaining the acoustic characteristic of the body 10 in accordance with the realized phase relations of the body 10. A portion to be examined is an interval between a depth Z1 and a depth Z2 deeper than Z1 within the body 10. Initially, the phase relation A is realized at the portion to be examined. In the signal analysis section 5, the frequency analysis is performed for the receptions signals corresponding to the depths Z1 and Z2. In the process of obtaining the acoustic characteristic of the body 10, the transfer characteristic calculating section 253 obtains the frequency characteristic of the reception signal. Here, the frequency characteristic of the reception signal corresponding to the depth Z1 in the phase relation A is expressed as A(Z1), the frequency characteristic of the reception signal corresponding to the depth Z2 is expressed as A(Z2), the frequency characteristic of the reception signal corresponding to the depth Z1 in the phase relation B is expressed as B(Z1) and the frequency characteristic of the reception signal corresponding to the depth Z2 is expressed as B(Z2). These frequency characteristics can be expressed as follows using the transmission frequency characteristic T of the second ultrasonic pulse, the frequency characteristic S of the ultrasonic scattering, and the propagation characteristic G.

$$A(Z1) = T^A(Z1) \cdot S(Z1) \cdot G(Z1) \quad (30)$$

$$B(Z1) = T^B(Z1) \cdot S(Z1) \cdot G(Z1) \quad (31)$$

$$A(Z2) = T^A(Z2) \cdot S(Z2) \cdot G(Z2) \quad (32)$$

$$B(Z2) = T^B(Z2) \cdot S(Z2) \cdot G(Z2) \quad (33)$$

Since in the phase relation A the second ultrasonic pulse is compressed, the frequency characteristic $T^A$ thereof is varied to the high-frequency side. On the other hand, in the phase relation B, the frequency characteristic $T^B$ of the second ultrasonic pulse is varied to the low-frequency side. Furthermore, because of the influence of the frequency dependence attenuation of the ultrasonic wave within the body 10, the frequency characteristics $T^A(Z2)$ and $T^B(Z2)$ on the depth Z1 are varied to the low-frequency side as compared with the frequency characteristics $T^A(Z1)$ and $T^B(Z1)$ on the depth Z1. If it is possible to measure the variation amount of the frequency characteristic due to the ultrasonic wave attenuation, this allows to obtain the ultrasonic attenuation characteristic of the body 10 to be examined. However, since the frequency dependency of the ultrasonic wave scattering characteristic S is extremely great, this method results in great error. In order to remove the influence of this scattering characteristic, with regard to the equations (30) to (33), the frequency characteristic ratios R are obtained to cancel the scattering characteristic S. That is, R are calculated in accordance with the following equations.

$$R(Z1) = A(Z1)/B(Z1) = T^{A(Z1)/TB(Z1)} \quad (34)$$
$$R(Z2) = A(Z2)/B(Z2) = T^{A(Z2)/TB(Z2)} \quad (35)$$

Since the variation amounts of the frequency characteristic ratios R(Z1) and R(Z2) corresponding to the depths to be examined on the frequency axis are equal to the variation amounts of the central frequencies of the frequency characteristics $T^A$ and $T^B$ corresponding to the depths to be examined, it is possible to obtain the attenuation characteristic of the ultrasonic wave within the body 10 on the basis of the variation amounts of the frequency characteristic ratios R. The calculations of the equations (34) and (35) are performed in the after-processing section 257 to obtain the attenuation factor on the basis of the variation amounts of the frequency characteristic ratios, which is in turn indicated on the indication section 8. The attenuation factor may be also obtained in accordance with a corresponding table between the variation amount of the frequency characteristic ratio and the attenuation factor which has been prepared in advance.

As obvious from the above description, according to this embodiment, initially measured are the phase in the case of only the second ultrasonic pulse, the phase in the case that the first and second ultrasonic pulses are superimposed in a phase relation and the phase in the case that they are superimposed in a phase relation which is shifted by 90° (for example) from the phase relation, whereby the first and second ultrasonic pulses can be superimposed in desirable phase relations such as phase relation A and phase relation B on the depth Z1. Therefore, to obtain the maximum variation amount of the frequency characteristic ratio R on the frequency axis due to the influence of the amplitude dependence distortion allows accurately measuring the ultrasonic wave attenuation characteristic without being subjected to the influence of the ultrasonic scattering characteristic within the body. In this embodiment, the signal analysis section accurately controls the phase relation of the first and second ultrasonic pulses superimposed within the body and the ultrasonic attenuation characteristic and so on of the body are measured using the influence of the amplitude dependence distortion of the two pulses, thus resulting in accurately controlling the phase relation of the first and second ultrasonic pulses even in the body having a complex acoustic characteristic and resulting in the accurate measurement of the acoustic characteristics. The effect is great. This embodiment may be also employed for examination of meat for food and the organism tissue.

Figure 10C:
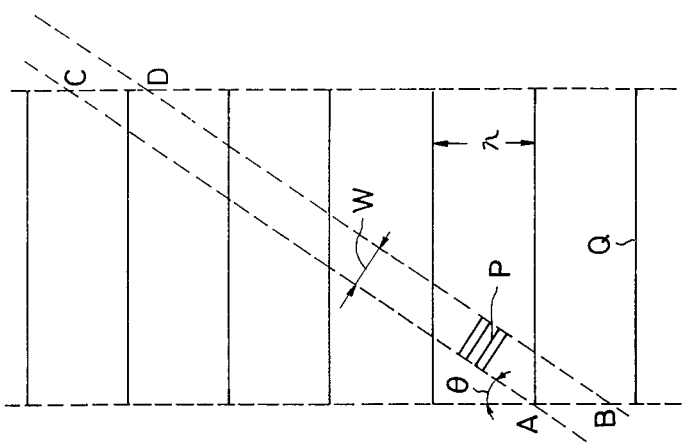
FIGS. 10A, 10B and 10C are illustrations for describing an arrangement for ultrasonic transducers.
Figure 10B:
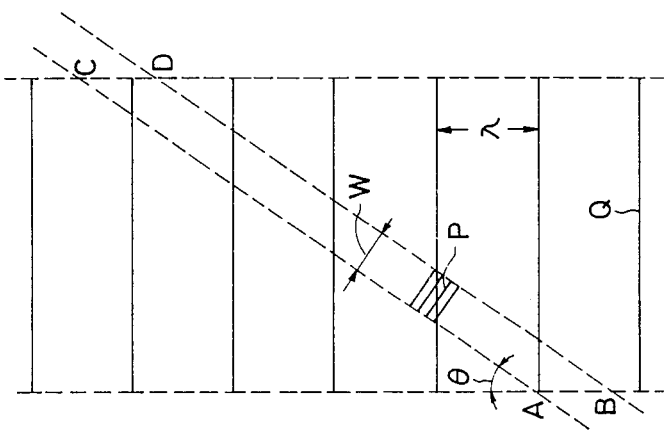
Figure 10A:
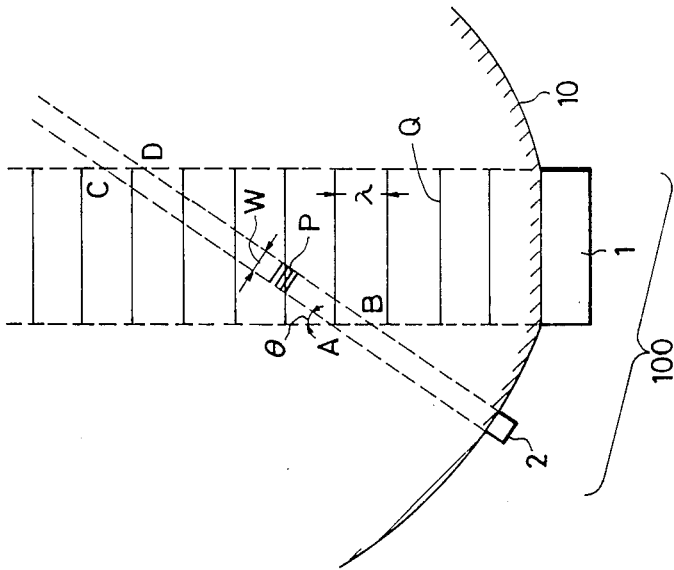
Figure 11A:
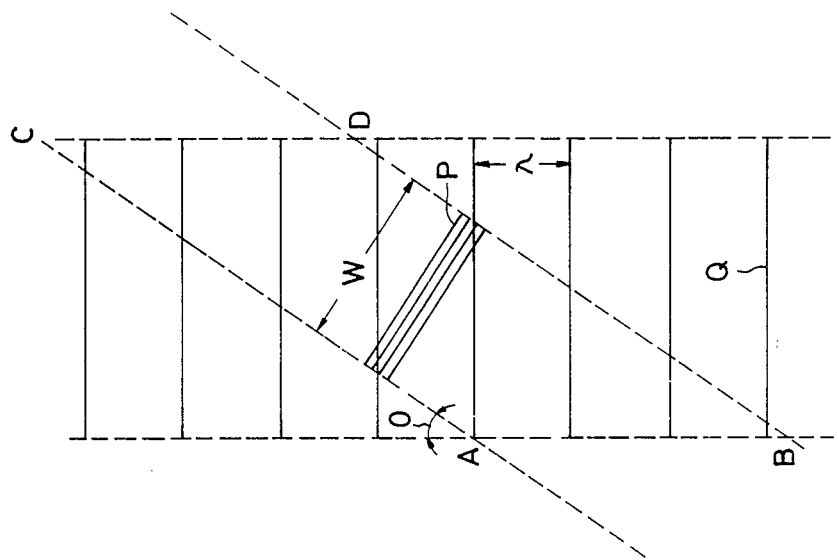
FIGS. 11 A and 11B are illustrations for describing operation with comparison.
Figure 11B:
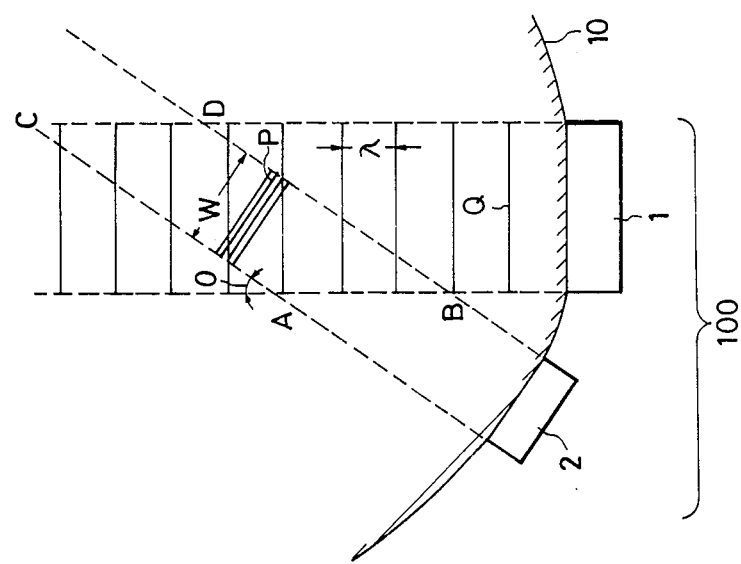

A description of the ultrasonic transducers employed for the above-mentioned embodiments of the present invention will be described hereinbelow with reference to FIGS. 10A to 10C. FIG. 10A is an illustration of an arrangement of an ultrasonic transducing apparatus and FIGS. 10B and 10C are illustrations for describing the operation of the ultrasonic transducer. In FIG. 10A, the ultrasonic transducing apparatus 100 comprises first and second ultrasonic transducers 1 and 2. Operation will be described hereinbelow. The first ultrasonic transducer 1 generates a first ultrasonic wave whose frequency is relatively low (for example 0.3 MHz). Character Q represents a wave surface of a high-pressure portion of the first ultrasonic wave and λ designates a wave length. The second ultrasonic transducer 2 generates a second ultrasonic wave whose frequency (for example 3 MHz) is higher than that of the first ultrasonic wave. Character P represents the second ultrasonic pulse comprising a short wave flux, for example, corresponding to four times of the wave length here. The second ultrasonic wave pulse has a beam width of W and is intercrossed with the first ultrasonic wave at portions, indicated at characters A, B, C, D, within the body to be examined. FIGS. 10B and 10C shows expansion of the intercrossed portions. In FIG. 10B, the second ultrasonic pulse P is positioned at the phase superimposed on a high-pressure portion of the wave surface of the first ultrasonic wave. In the body 10 such as organism, because of non-linear effect, the wave velocity of the high-pressure portion generally becomes high as compared with that of the low-pressure portion. Thus, in the above-mentioned phase, the second ultrasonic pulse P is accelerated and hence in the second ultrasonic pulse returning by reflection from the portion to be examined, the delay time becomes shorter by a value corresponding to the acceleration. On the other hand, in the case of the phase shown in FIG. 10C, i.e., in the case that the second ultrasonic pulse P is positioned at a low-pressure phase at a trough portion of the wave surface of the first ultrasonic wave, it is reversely decelerated and the delay time becomes longer. That is, it is possible to measure a non-linear parameter, being the degree of the non-linearity, by measuring the variation amount of the delay time with the phase. At this time, since the second ultrasonic pulse P has the beam width of W, if the phase relation does not become constant in the beam width W, in the second ultrasonic pulse P, the acceleration and deceleration partially occur, the variation amount of the delay time is varied as a whole, resulting in difficulty to perform a stable measurement. For example, as in illustrations of FIGS. 11A and 11B, the beam width of the second ultrasonic pulse P is wider. As shown in the expanded illustration of FIG. 11B, the beam width Q of the second ultrasonic pulse P is from the wave surface Q to the next wave surface Q, and therefore, a portion of the wave of the second ultrasonic pulse P is accelerated and other portion thereof is decelerated, resulting in the fact that the whole is not significantly varied. That is, the measurement cannot be performed stably by means of the ultrasonic apparatus for producing such waves. Therefore, for obtaining the result that the phase relation substantially becomes constant with respect to the entire beam width W of the second ultrasonic pulse P, it is required to satisfy the following equation (36).

$$\tan \theta \leq \frac{\lambda}{2W} \tag{36}$$

Here, $\theta$ is an angle made by the propagating direction of the first ultrasonic wave and the propagating direction of the second ultrasonic wave, $\lambda$ represents the wave length of the first ultrasonic wave, and the above equation (36) expresses the fact that the error of the position of phase in the beam width W of the second ultrasonic pulse P is below $\lambda/2$. That is, in the above-mentioned embodiment of the ultrasonic transducing apparatus, the first and second ultrasonic transducers 1, 2 are arranged so as to satisfy the conditions of the equation (36). In the case that the ultrasonic beam has a gentle distribution, it is appropriate that the beam width is a width from the maximum value of the sound pressure of the center portion to the sound pressure reduced by 3 db therefrom.

Figure 12:
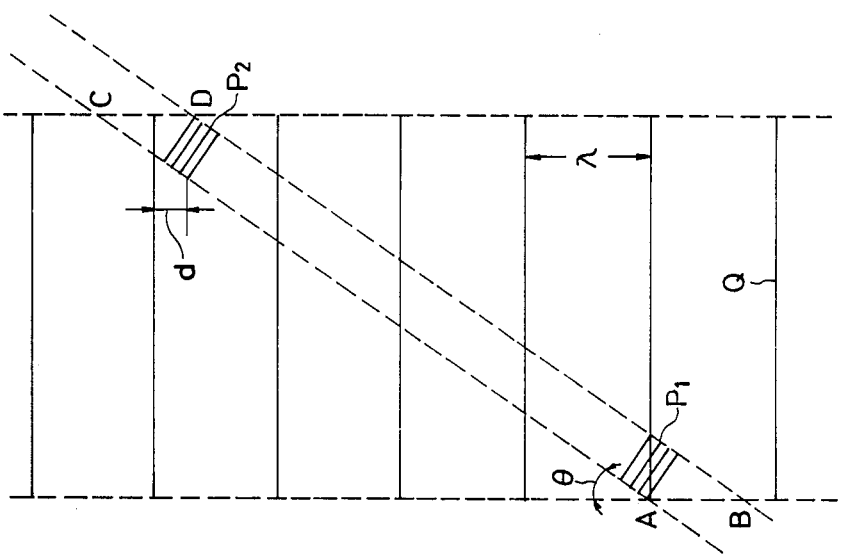
FIG. 12 is an illustration for describing another arrangement for the ultrasonic transducers.

A description will be made hereinbelow in terms of another embodiment of the ultrasonic transducing apparatus. FIG. 12 is an illustration for describing an operation thereof. In this embodiment, the first and second ultrasonic transducers 1 and 2 of FIG. 10A are arranged so that the angle $\theta$ made by the propagating directions of the first ultrasonic wave and the second ultrasonic pulse satisfies a specific condition. As shown in FIG. 12, the second ultrasonic pulse, as indicated by character P1, is positioned at a phase coincident with the high-pressure wave surface Q of the first ultrasonic wave at the start portion of intersection, and when it is advanced to a position indicated by P2 by propagation, generally, the position is not coincident with the wave surface Q of the first ultrasonic wave, resulting in occurrence of an error d. When this error is small, the phase relation becomes more stable to improve the stability of the measurement. For preventing the occurrence of this error d, it is required that the angle $\theta$ of the propagating directions of the first ultrasonic wave and the second ultrasonic pulse satisfies the condition of the following equation (37). This is obtained in accordance with a geometrical consideration.

$$\theta = \cos^{-1}(C1/C2) \tag{37}$$

where C1 is the phase velocity of the first ultrasonic wave and C2 is the group velocity of the second ultrasonic pulse. So as to satisfy this condition, the first ultrasonic transducer 1 and the second ultrasonic transducer 2 are arranged, whereby the phase relation is not varied due to the propagation of the second ultrasonic pulse. Thus, for obtaining the above-mentioned effect, the angle $\theta$ is required to be in the range of the following equation (38).

$$\tfrac{1}{2}\cos^{-1}(C1/C2) \leq \theta \leq 2\cos^{-1}(C1/C2) \qquad (38)$$

That is, in this embodiment, the first and second ultrasonic transducers 1 and 2 are arranged so that the angle $\theta$ is in the range of the equation (38).

In detail, when the frequency of the first ultrasonic wave is 0.3 MHz and the frequency of the second ultrasonic pulse is 3 MHz, in the body 10 such as organism, C1/C2 is estimated to be about 0.997 and $\cos^{-1}(C1/C2)$ (optimal angle) is estimated to be about 4.4. These values depend upon the class of the tissue.

Figure 13:
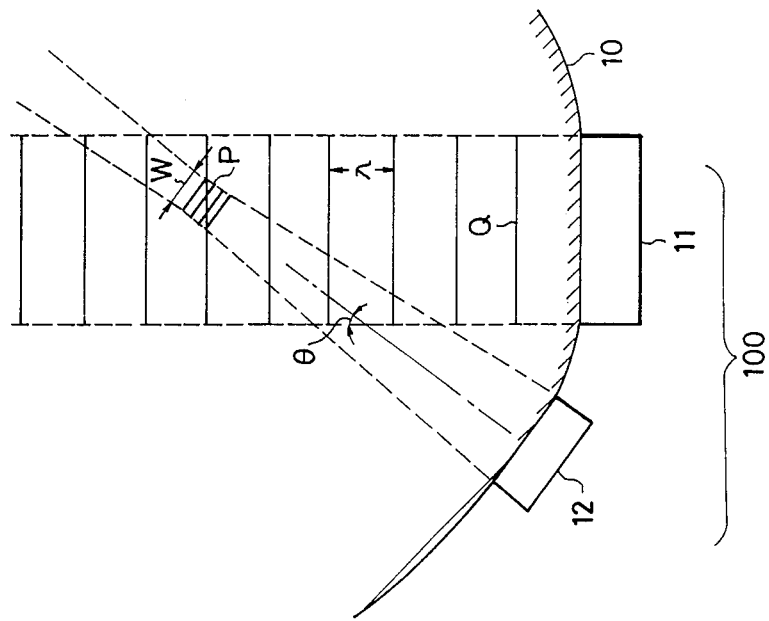
FIG. 13 is an illustration for describing a further arrangement for the ultrasonic transducers.

A further embodiment of the ultrasonic transducing apparatus will be described hereinbelow with reference to FIG. 13. As shown in FIG. 13, the difference of this embodiment with respect to the above-mentioned embodiment of FIG. 10A is that the second ultrasonic transducer is arranged so as to restrict the beam by means of an acoustic lens. Similarly, in this embodiment, when the minimum width of the second ultrasonic pulse at the intersection of the wave surface Q of the first ultrasonic wave and the second ultrasonic pulse P is W, a first ultrasonic transducer 11 and a second ultrasonic transducer 12 are arranged so as to satisfy the condition of the equation (36). According to this embodiment, it is possible to obtain a beam width W smaller than the diameter of the second ultrasonic transducer 12. Here, it is also appropriate that the first ultrasonic transducer 11 has an acoustic lens or the like to restrict the beam. The restriction of the beam may be achieved by driving a number of extremely small transducers with signals having electronic time delay, that is, by so-called electronic focus system. Furthermore, in this embodiment, it is also appropriate that the angle $\theta$ is determined so as to satisfy the condition of the equation (38).

Figure 14A:
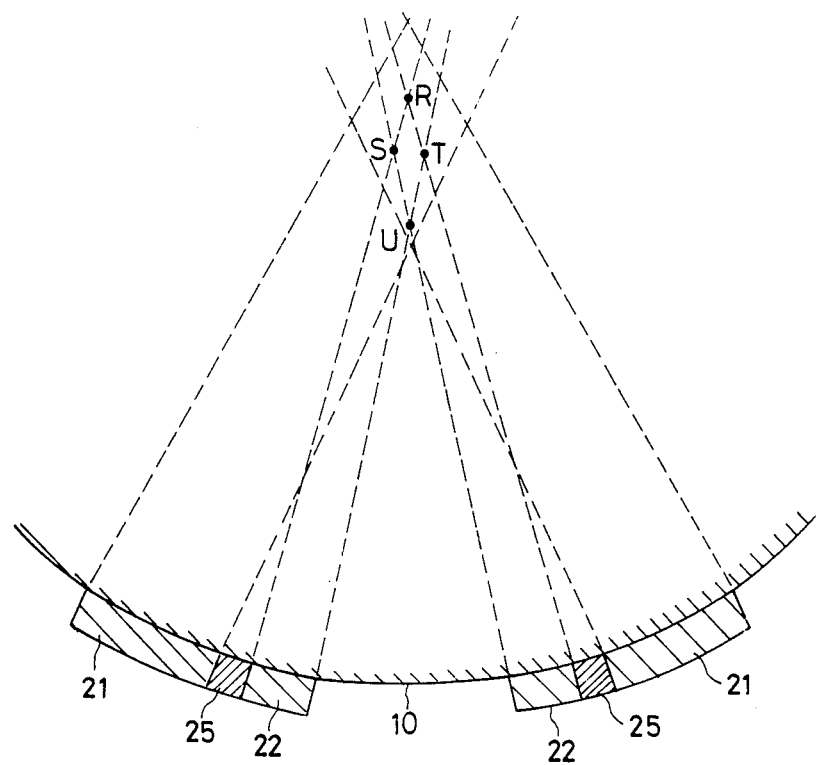
FIGS. 14A, 14B, 15A and 15B are illustrations for describing a still further arrangement for the ultrasonic transducers.
Figure 14B:
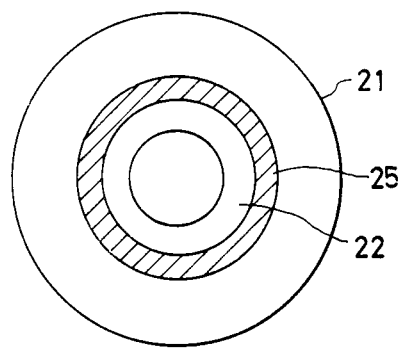
Figure 15A:
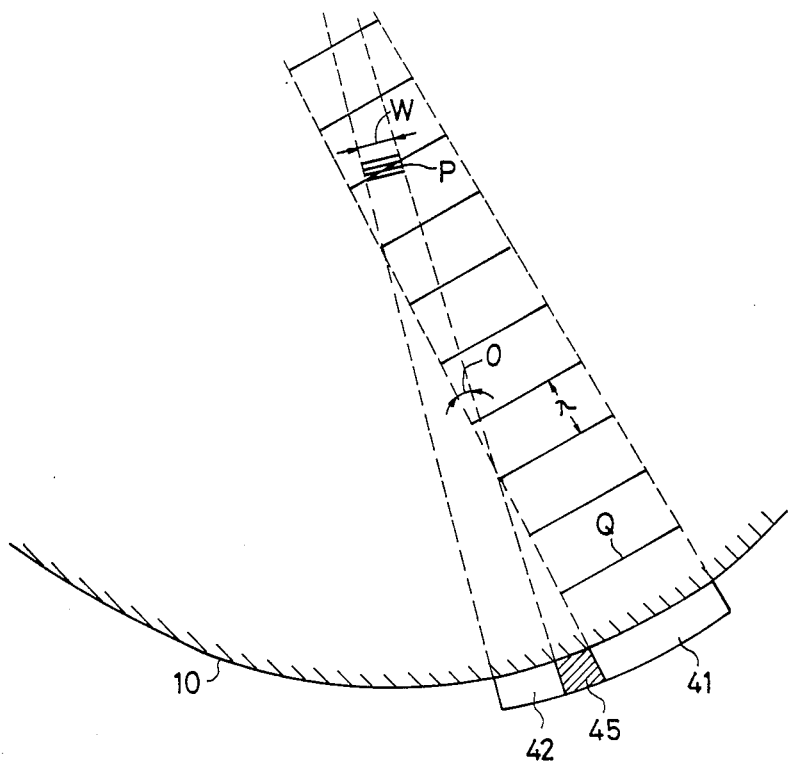
Figure 15B:
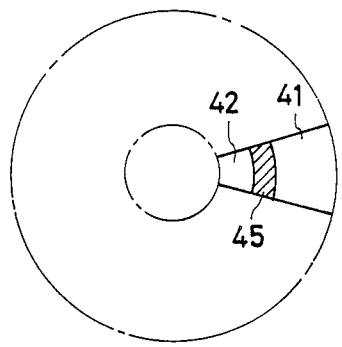

A still further embodiment of the ultrasonic transducing apparatus according to the present invention will be described hereinbelow with reference to FIGS. 14A and 14B. As shown in FIGS. 14A and 14B, the difference of this embodiment with respect to the above-mentioned embodiment of FIG. 10A is that first and second ultrasonic transducers 21 and 22 are coaxially coupled to each other with a coupling material 25 being interposed therebetween. According to this embodiment, the first ultrasonic wave due to the first ultrasonic transducer 21 and the second ultrasonic pulse due to the second ultrasonic transducer 22 are collected at center portions R, S, T, U within the body 10. The operation of this embodiment will be understood from FIG. 15A and 15B. An arrangement shown in FIGS. 15A and 15B is of a portion taken out from the coaxial arrangement of the first and second ultrasonic transducers 21 and 22 so as to comprise a first ultrasonic transducer 41, a second ultrasonic transducer 42 and a coupling material 45 provided therebetween. This arrangement corresponds to the arrangement of FIG. 13. That is, in FIG. 15A, the first ultrasonic transducer 41 and the second ultrasonic transducer 42 are arranged so that the beam width W, angle $\theta$, wave length $\lambda$ and so on are set so as to satisfy the equation (36). It is considered that the embodiment of FIG. 14A and 14B corresponds to a combination of a plurality of apparatus of FIGS. 15A and 15B. That is, it is also appropriate to collect a plurality of apparatus each satisfying the equation (36). If in this embodiment the condition of the equation (38) can be satisfied, the apparatus of this embodiment can obtain the same effect.

As described above, since the arrangement is made so as to satisfy the relation of $\tan\theta \leq \lambda(2W)$ among the wave length $\lambda$ of the first ultrasonic wave transmitted by the first ultrasonic transducer, the beam width W of the second ultrasonic pulse whose frequency is higher than that of the first ultrasonic wave and which is transmitted by the second ultrasonic transducer, and the propagating angle $\theta$ of the first ultrasonic wave and the second ultrasonic pulse, it is possible that the phase relation of the second ultrasonic pulse with respect to the first ultrasonic wave is not varied spacially, thus resulting in stable measurement of the nonlinear parameter of the body to be examined.

It should be understood that the foregoing relates to only preferred embodiments of the invention, and that it is intended to cover all changes and modifications of the embodiments of this invention herein used for the purposes of the disclosure, which do not constitute departures from the spirit and scope of the invention.

What is claimed is:

1. An ultrasonic examination apparatus comprising:
    ultrasonic transducing means for transmitting first and second ultrasonic pulses into a body to be examined, the frequency of said second ultrasonic pulse being higher than that of said first ultrasonic pulse, said first and second ultrasonic pulses being superimposed on each other at a predetermined portion within said body after the transmissions, and said ultrasonic transducing means receiving an echo signal due to reflection of said first and second ultrasonic pulses in said body;
    drive means coupled to said ultrasonic transducing means for driving said ultrasonic transducing means so that said first and second ultrasonic pulse are transmitted from said ultrasonic transducing means;
    control means coupled to said drive means for energizing said drive means so as to control the phase of said first and second ultrasonic pulses to be transmitting therefrom, said control means being coupled to said ultrasonic transducing means to be responsive to said echo reception signal for determining the phase relation therebetween so that the modulation characteristic of said echo signal is varied at a maximum, said control means obtaining information within said body on the basis of said echo reception signals with the variation of the modulation characteristic thereof being at a maximum.

2. An ultrasonic examination apparatus as claimed in claim 1, wherein the maximum variation of the modulation characteristic for determining the phase relation between said first and second ultrasonic pulses corresponds to a maximum ratio between two spectrums of the two echo reception signals obtained under the condition of the two different phase relations between said first and second ultrasonic pulses transmitted from said ultrasonic transducing means.

3. An ultrasonic examination apparatus as claimed in claim 1, wherein the maximum variation of the modulation characteristic for determining the phase relation between said first and second ultrasonic pulses corresponds to a maximum phase shift between two spectrums of the two echo reception signals obtained under the condition of the two different phase relations between said first and second ultrasonic pulses transmitted from said ultrasonic transducing means.

4. An ultrasonic examination apparatus as claimed in claim 1, wherein, when a height of said second ultrasonic pulse at the predetermined portion at which said first and second ultrasonic pulses are superimposed on each other is W, an angle made by a propagating direction of said first ultrasonic pulse and a propagating direction of said second ultrasonic pulse into said body is $\theta$ and a wave length of said first ultrasonic pulse is $\lambda$, said ultrasonic transducing means is arranged so as to satisfy the following condition:

$$\tan \theta \leq \frac{\lambda}{2W}$$

5. An ultrasonic examination apparatus as claimed in claim 4, wherein, when a phase velocity of said first ultrasonic pulse is C1, a group velocity of said second ultrasonic pulse is C2, the angle $\theta$ of the propagating directions of said first and second ultrasonic pulses is determined so as to satisfy the following condition:

$$\tfrac{1}{2}\cos^{-1}(C1/C2) \leq \theta \leq 2\cos^{-1}(C1/C2)$$

6. An ultrasonic examination apparatus as claimed in claim 5, wherein said ultrasonic transducing means comprises a plurality of ultrasonic transducers each transmitting said first and second ultrasonic pulses.

7. An ultrasonic examination apparatus as claimed in claim 1, wherein said second ultrasonic pulse is superimposed on a portion of said first ultrasonic pulse at which its particle velocity is positively or negatively peaked.

8. An ultrasonic examination apparatus as claimed in claim 1, wherein said second ultrasonic pulse is superimposed on a portion of said first ultrasonic pulse at which its particle acceleration is positively or negatively peaked.

9. An ultrasonic examination apparatus as claimed in claim 1, wherein the maximum variation of the modulation characteristic for determining the phase relation between said first and second ultrasonic pulses corresponds to a maximum ratio between two spectrums of the two echo reception signals obtained under the condition of the two different phase relations between said first and second ultrasonic pulses transmitted from said ultrasonic transducing means and a maximum phase shift between two spectrums of the two echo reception signals obtained under the condition of the two different phase relations.

10. An ultrasonic examination apparatus comprising:
first ultrasonic transducing means for transmitting a first ultrasonic pulse into a body to be examined;
second ultrasonic transducing means for transmitting into said body a second ultrasonic pulse whose frequency is higher than that of said first ultrasonic pulse, said second ultrasonic pulses being superimposed on said first ultrasonic pulses at a predetermined portion within said body after the transmissions, and said second ultrasonic transducing means receiving an echo signal due to reflection in said body;
first and second drive means respectively coupled to said first and second ultrasonic transducing means for driving said first and second ultrasonic transducing means so that said first and second ultrasonic pulses are transmitted from said ultrasonic transducing means into said body;
control means coupled to said first and second drive means for controlling the timing of energization of said first and second drive means so as to control a phase relationship between said first and second ultrasonic pulses to be transmitted therefrom, said control means being coupled to said ultrasonic transducing means to be responsive to the echo reception signals and energizing said first and second drive means plural times at different timings so as to successively change the phase relation between said first and second ultrasonic pulses for measuring the differences between frequency characteristics of the successive echo reception signals to determine the phase relation therebetween at which the variation in the frequency characteristic is at a maximum, said control means obtaining information within said body on the basis of said echo reception signals under the condition of the phase relation therebetween in which the frequency characteristic is varied at a maximum.

11. An ultrasonic examination apparatus as claimed in claim 10, wherein the maximum variation of the frequency characteristic for determining the phase relation between said first and second ultrasonic pulses corresponds to a maximum ratio between two spectrums of the two echo reception signals obtained under the condition of the two different phase relations between said first and second ultrasonic pulses transmitted from said ultrasonic transducing means.

12. An ultrasonic examination apparatus as claimed in claim 10, wherein the maximum variation of the frequency characteristic for determining the phase relation between said first and second ultrasonic pulses corresponds to a maximum phase shift between two spectrums of the two echo reception signals obtained under the condition of the two different phase relations between said first and second ultrasonic pulses transmitted from said ultrasonic transducing means.

13. An ultrasonic examination apparatus as claimed in claim 10, wherein, when a height of said second ultrasonic pulse at the predetermined portion at which said first and second ultrasonic pulses are superimposed on each other is W, an angle made by a propagating direction of said first ultrasonic pulse and a propagating direction of said second ultrasonic pulse into said body is $\theta$, and a wave length of said first ultrasonic pulse is $\lambda$, said ultrasonic transducing means is arranged so as to satisfy the following condition:

$$\tan \theta \leq \frac{\lambda}{2W}$$

14. An ultrasonic examination apparatus as claimed in claim 13, wherein, when a phase velocity of said first ultrasonic pulse is C1, a group velocity of said second ultrasonic pulse is C2, the angle 0 of the propagating directions of said first and second ultrasonic pulses is determined so as to satisfy the following condition:

$$\tfrac{1}{2}\cos^{-1}(C1/C2) \leq \theta \leq 2\cos^{-1}(C1/C2)$$

15. An ultrasonic examination apparatus as claimed in claim 14, wherein each of said first and second ultrasonic transducing means comprises a plurality of ultrasonic transducers each transmitting said first or second ultrasonic pulse.

16. An ultrasonic examination apparatus comprising:

first ultrasonic transducing means for transmitting a first ultrasonic pulse into a body to be examined;

second ultrasonic transducing means for transmitting into said body a second ultrasonic pulse whose frequency is higher than that of said first ultrasonic pulse, said second ultrasonic pulses being superimposed on said first ultrasonic pulses within said body after the transmissions, and said second ultrasonic transducing means receiving an echo signal due to refection in said body;

first and second drive means respectively coupled to said first and second ultrasonic transducing means for driving said first and second ultrasonic transducing means so that said first and second ultrasonic pulses are transmitted from said ultrasonic transducing means into said body;

control means coupled to said first and second drive means for controlling the timing of energization of said first and second drive means so as to control a phase relation between said first and second ultrasonic pulses to be transmitted therefrom, said control means being coupled to said ultrasonic transducing means to be responsive to the echo reception signal and energizing said first and second drive means plural times at different timings so as to successively change the phase relation between said first and second ultrasonic pulses, said control means successively measuring frequency characteristics of the echo reception signals from a first depth within said body and further successively measuring frequency characteristics of the echo reception signals from a second depth therewithin to determine the phase relation therebetween in which the difference between the frequency characteristics for said first and second depths is at a maximum, said control means obtaining information within said body on the basis of said echo reception signals under the condition of the phase relation therebetween in which the difference of the frequency characteristic is at a maximum.

17. An ultrasonic examination apparatus as claimed in claim 16, wherein the maximum difference between the frequency characteristics at said first and second depths for determining the phase relation between said first and second ultrasonic pulses corresponds to a maximum ratio between two spectrums of the two echo reception signals from said first and second depths.

18. An ultrasonic examination apparatus as claimed in claim 16 wherein the maximum difference between the frequency characteristic at said first and second depths for determining the phase relation between said first and second ultrasonic pulses corresponds to the maximum phase shift amount between two spectrums of the two echo reception signals from said first and second depths.

19. An ultrasonic examination apparatus as claimed in claim 16, wherein, when a height of said second ultrasonic pulse at the predetermined portion at which said first and second ultrasonic pulses are superimposed on each other is W, an angle made by a propagating direction of said first ultrasonic pulse and a propagating direction of said second ultrasonic pulse into said body is $\theta$, and a wave length of said first ultrasonic pulse is $\lambda$, said ultrasonic transducing means is arranged so as to satisfy the following condition:

$$\tan \theta \leq \frac{\lambda}{2W}$$

20. An ultrasonic examination apparatus as claimed in claim 19, wherein, when a phase velocity of said first ultrasonic pulse is C1, a group velocity of said second ultrasonic pulse is C2, the angle $\theta$ of the propagating directions of said first and second ultrasonic pulses is determined so as to satisfy the following condition:

$$\tfrac{1}{2} \cos^{-1}(C1/C2) \leq \theta \leq 2 \cos^{-1}(C1/C2)$$

21. An ultrasonic examination apparatus as claimed in claim 19, wherein each of said first and second ultrasonic transducing means comprises a plurality of ultrasonic transducers each transmitting said first or second ultrasonic pulse.

22. An ultrasonic examination apparatus comprising:

ultrasonic transducing means for transmitting first and second ultrasonic pulses into a body to be examined, the frequency of said second ultrasonic pulse being higher than that of said first ultrasonic pulse, said first and second ultrasonic pulses being superimposed on each other at a predetermined portion within said body after the transmissions, and said ultrasonic transducing means receiving an echo signal due to reflection of said first and second ultrasonic pulses in said body;

drive means coupled to said ultrasonic transducing means for driving said ultrasonic transducing means so that said first and second ultrasonic pulses are transmitted from said ultrasonic transducing means;

control means coupled to said drive means for energizing said drive means so as to control phases of said first and second ultrasonic pulses to be transmitted therefrom, said control means being coupled to said ultrasonic transducing means to be responsive to said echo reception signal and controlling the phase relation therebetween so that said second ultrasonic pulse is superimposed on a portion of said first ultrasonic pulse at which its particle velocity is positively or negatively peaked, said control means obtaining information within said body on the basis of said echo reception signals in said controlled phase relation.

23. An ultrasonic examination apparatus comprising:

ultrasonic pulses into a body to be examined, the frequency of said second ultrasonic pulse being higher than that of said first ultrasonic pulse, said first and second ultrasonic pulses being superimposed on each other at a predetermined portion within said body after the transmissions, and said ultrasonic transducing means receiving an echo signal due to reflection of said first and second ultrasonic pulses in said body;

drive means coupled to said ultrasonic transducing means for driving said ultrasonic transducing means so that said first and second ultrasonic pulses are transmitted from said ultrasonic transducing means;

control means coupled to said drive means for energizing said drive means so as to control the phase of said first and second ultrasonic pulses to be transmitted therefrom, said control means being coupled to said ultrasonic transducing means to be responsive to said echo reception signal and controlling the phase relation therebetween so that said second ultrasonic pulse at which its particle acceleration is positively or negatively peaked, said control means obtaining information within said body on the basis of said echo reception signals in said controlled phase relation.

* * * * *